(12) United States Patent
Messerschmidt et al.

(10) Patent No.: US 11,371,882 B2
(45) Date of Patent: *Jun. 28, 2022

(54) POROUS MESH SPECTROMETRY METHODS AND APPARATUS

(71) Applicant: NUEON INC., Menlo Park, CA (US)

(72) Inventors: Robert Messerschmidt, Menlo Park, CA (US); Howland D.T. Jones, Rio Rancho, NM (US)

(73) Assignee: NUEON INC., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/947,971

(22) Filed: Aug. 26, 2020

(65) Prior Publication Data

US 2021/0041290 A1 Feb. 11, 2021

Related U.S. Application Data

(63) Continuation of application No. 16/137,012, filed on Sep. 20, 2018, now Pat. No. 10,760,965, which is a
(Continued)

(51) Int. Cl.
*G01J 3/02* (2006.01)
*G01N 21/03* (2006.01)
(Continued)

(52) U.S. Cl.
CPC ........... *G01J 3/0267* (2013.01); *G01J 3/0264* (2013.01); *G01N 21/03* (2013.01);
(Continued)

(58) Field of Classification Search
CPC ...... G01J 3/0267; G01J 3/0264; G01N 33/49; G01N 21/25; G01N 21/03; G01N 21/552;
(Continued)

(56) References Cited

U.S. PATENT DOCUMENTS 4,514,050 A   4/1985 Stites
4,775,637 A   10/1988 Sutherland
(Continued)

FOREIGN PATENT DOCUMENTS

EP   0476192   3/1992
EP   2700933   2/2014
(Continued)

OTHER PUBLICATIONS

"International Search Report and Written Opinion dated Nov. 7, 2016 for International PCT Patent Application No. PCT/US2016/026825".

(Continued)

*Primary Examiner* — Dominic J Bologna
(74) *Attorney, Agent, or Firm* — FisherBroyles LLP; John Shimmick

(57) ABSTRACT

Described herein are methods and apparatus for spectroscopic analysis of samples. In many embodiments, an apparatus for providing spectroscopic analysis of a sample comprises a sample holder. For example, the sample holder may comprise a consumable single use sample holder that can be readily coupled to and removed from a measurement apparatus such as a spectrometer. The sample holder may comprise a measurement surface configured to receive the sample during measurement, wherein the measurement surface may comprise a porous mesh. The porous mesh can receive the sample to optimally configure the sample for spectroscopic measurement, as described in further detail herein.

24 Claims, 19 Drawing Sheets

Related U.S. Application Data continuation of application No. PCT/US2017/023389, filed on Mar. 21, 2017.

(60) Provisional application No. 62/310,954, filed on Mar. 21, 2016.

(51) Int. Cl.
  *G01N 21/552* (2014.01)
  *G01N 21/25* (2006.01)
  *G01N 33/49* (2006.01)

(52) U.S. Cl.
  CPC ......... *G01N 21/0303* (2013.01); *G01N 21/25* (2013.01); *G01N 21/552* (2013.01); *G01N 33/49* (2013.01); *G01N 2021/035* (2013.01); *G01N 2021/0339* (2013.01); *G01N 2021/0346* (2013.01)

(58) Field of Classification Search
  CPC ......... G01N 21/0303; G01N 2021/035; G01N 2021/0346; G01N 2021/0339
  See application file for complete search history.

(56) References Cited

U.S. PATENT DOCUMENTS

| | | | |
|---|---|---|---|
| 4,882,492 A | 11/1989 | Schlager | |
| 4,975,581 A | 12/1990 | Robinson | |
| 5,200,609 A | 4/1993 | Sting | |
| 5,235,409 A | 8/1993 | Burgi | |
| 5,280,786 A | 1/1994 | Wlodarczyk | |
| 5,288,646 A | 2/1994 | Lundsgaard | |
| 5,327,777 A | 7/1994 | Kaye | |
| 5,331,958 A | 7/1994 | Oppenheimer | |
| 5,362,445 A | 11/1994 | Miyahara | |
| 5,366,903 A | 11/1994 | Lundsgaard | |
| 5,437,840 A | 8/1995 | King | |
| 5,525,518 A | 6/1996 | Lundsgaard | |
| 5,599,959 A | 2/1997 | Hosmane | |
| 5,636,640 A | 6/1997 | Staehlin | |
| 5,689,333 A | 11/1997 | Batchelder | |
| 5,706,208 A | 1/1998 | Osten | |
| 5,729,333 A | 3/1998 | Osten | |
| 5,830,133 A | 11/1998 | Osten | |
| 6,006,119 A | 12/1999 | Soller | |
| 6,141,100 A | 10/2000 | Burka | |
| 6,266,139 B1 | 7/2001 | Mannhardt | |
| 6,285,448 B1 | 9/2001 | Kuenstner | |
| 6,353,471 B1 | 3/2002 | Samsoondar | |
| 6,383,179 B1 | 5/2002 | Neuberger | |
| 6,603,987 B2 | 8/2003 | Whitson | |
| 6,614,730 B1 | 9/2003 | Vo-Dinh | |
| 6,638,769 B2 | 10/2003 | Lilja | |
| 6,676,903 B2 | 1/2004 | Potyrailo | |
| 6,788,394 B1 | 9/2004 | Garcia-Rubio | |
| 6,791,674 B2 | 9/2004 | Kawano | |
| 6,866,675 B2 | 3/2005 | Perez | |
| 6,944,487 B2 | 9/2005 | Maynard | |
| 7,001,344 B2 | 2/2006 | Freeman | |
| 7,004,928 B2 | 2/2006 | Aceti | |
| 7,150,755 B2 | 12/2006 | LeVaughn | |
| 7,271,912 B2 | 9/2007 | Sterling | |
| 7,282,105 B1 | 10/2007 | Plunkett | |
| 7,291,497 B2 | 11/2007 | Holmes | |
| 7,299,711 B1 | 11/2007 | Linker | |
| 7,319,894 B2 | 1/2008 | Higgins | |
| 7,426,407 B2 | 9/2008 | Higgins | |
| 7,570,357 B2 | 8/2009 | Tsenkova | |
| 7,593,108 B2 | 9/2009 | Sterling | |
| 7,656,523 B2 | 2/2010 | Sun | |
| 7,787,109 B2 | 8/2010 | Dosmann | |
| 7,869,009 B2 | 1/2011 | Dosmann | |
| 7,969,307 B2 | 6/2011 | Peeters | |
| 8,033,898 B2 | 10/2011 | McNaughto et al. | |
| 8,041,538 B2 | 10/2011 | Meyer | |
| 8,077,042 B2 | 12/2011 | Peeters | |
| 8,160,665 B2 | 4/2012 | Mischler | |
| 8,184,273 B2 | 5/2012 | Dosmann | |
| 8,206,650 B2 | 6/2012 | Samsoondar | |
| 8,303,518 B2 | 11/2012 | Aceti | |
| 8,483,789 B2 | 7/2013 | Higgins | |
| 8,690,798 B2 | 4/2014 | Douglas | |
| 8,808,202 B2 | 8/2014 | Brancazio | |
| 8,821,412 B2 | 9/2014 | Gonzalez-Zugasti | |
| 8,821,413 B2 | 9/2014 | Effenhauser | |
| 8,830,449 B1 | 9/2014 | Lamego | |
| 8,900,514 B2 | 12/2014 | Forsell | |
| 9,113,836 B2 | 8/2015 | Bernstein | |
| 9,133,024 B2 | 9/2015 | Phan | |
| 9,217,706 B2 | 12/2015 | Mucci | |
| 9,259,175 B2 | 2/2016 | Stafford | |
| 9,291,504 B2 | 3/2016 | Goldring | |
| 9,341,515 B2 | 5/2016 | Schulte | |
| 9,377,396 B2 | 6/2016 | Goldring et al. | |
| 9,470,673 B2 | 10/2016 | Samsoondar | |
| 9,470,699 B2 | 10/2016 | Peeters | |
| 9,603,562 B2 | 3/2017 | Aceti | |
| 10,337,984 B2 | 7/2019 | Messerschmidt | |
| 10,760,965 B2 * | 9/2020 | Messerschmidt | G01N 33/49 |
| 2002/0122168 A1 | 9/2002 | Grcia-Rubio | |
| 2002/0123677 A1 | 9/2002 | Miki | |
| 2002/0156380 A1 | 10/2002 | Feld | |
| 2003/0018282 A1 | 1/2003 | Effenhauser | |
| 2003/0059948 A1 | 3/2003 | Hildenbrand | |
| 2003/0083686 A1 | 5/2003 | Freeman | |
| 2003/0171696 A1 | 9/2003 | Dosmann | |
| 2003/0175160 A1 | 9/2003 | Archibald | |
| 2003/0189707 A1 | 10/2003 | Naya | |
| 2003/0227628 A1 | 12/2003 | Kreimer | |
| 2004/0186359 A1 | 9/2004 | Beaudoin | |
| 2005/0208501 A1* | 9/2005 | Goldrick | C12Q 1/6806 435/6.14 |
| 2005/0244952 A1* | 11/2005 | Cohen | G01N 21/76 435/287.2 |
| 2006/0043301 A1 | 3/2006 | Mantele | |
| 2006/0057554 A1 | 3/2006 | Watling | |
| 2006/0057642 A1 | 3/2006 | Kiefer | |
| 2006/0074282 A1 | 4/2006 | Ward | |
| 2006/0135861 A1 | 6/2006 | Lucassen | |
| 2006/0166302 A1 | 7/2006 | Clarke | |
| 2007/0076208 A1 | 4/2007 | Koo | |
| 2007/0134738 A1 | 6/2007 | Wells | |
| 2007/0213636 A1 | 9/2007 | Kuriger | |
| 2008/0138793 A1 | 6/2008 | Lindberg | |
| 2008/0153171 A1 | 6/2008 | Liu | |
| 2008/0218734 A1 | 9/2008 | Higashi | |
| 2008/0218736 A1 | 9/2008 | Shaw | |
| 2008/0300508 A1 | 12/2008 | Tomer | |
| 2010/0105098 A1 | 4/2010 | Frederiske | |
| 2010/0121163 A1 | 5/2010 | Vestel | |
| 2010/0129919 A1 | 5/2010 | Levin | |
| 2010/0142773 A1 | 6/2010 | Cha | |
| 2010/0196945 A1 | 8/2010 | Forsell | |
| 2010/0245803 A1 | 9/2010 | Samsoondar | |
| 2010/0256524 A1 | 10/2010 | Levinson | |
| 2010/0284004 A1 | 11/2010 | Reich | |
| 2011/0003707 A1 | 1/2011 | Goix | |
| 2011/0020849 A1 | 1/2011 | Spence | |
| 2011/0105952 A1 | 5/2011 | Bernstein | |
| 2011/0111435 A1 | 5/2011 | Dobson | |
| 2011/0144463 A1 | 6/2011 | Pesach | |
| 2011/0172508 A1 | 7/2011 | Chickering | |
| 2011/0196239 A1 | 8/2011 | Behrend | |
| 2011/0223654 A1 | 9/2011 | Holman | |
| 2011/0278472 A1 | 11/2011 | Atzler | |
| 2011/0287948 A1 | 11/2011 | Suresh | |
| 2012/0016818 A1 | 1/2012 | Hackett | |
| 2012/0088486 A1 | 4/2012 | Messerchmidt | |
| 2012/0142559 A1 | 6/2012 | Tuytten | |
| 2012/0205727 A1 | 8/2012 | Kanakasabapathy | |
| 2012/0257199 A1 | 10/2012 | Liu | |
| 2012/0261256 A1 | 10/2012 | Chang | |
| 2012/0271125 A1 | 10/2012 | Bernstein | |

(56) References Cited

U.S. PATENT DOCUMENTS

| | | | |
|---|---|---|---|
| 2012/0274934 | A1 | 11/2012 | Messerschmidt |
| 2013/0143226 | A1 | 6/2013 | Hill |
| 2013/0338013 | A1* | 12/2013 | Zhong ............... C12Q 1/68 |
| | | | 506/3 |
| 2014/0112568 | A1 | 4/2014 | Liu |
| 2014/0148669 | A1 | 5/2014 | Saban |
| 2014/0336534 | A1 | 11/2014 | Balligand |
| 2014/0336536 | A1 | 11/2014 | Brancazio |
| 2015/0055121 | A1 | 2/2015 | Forsell |
| 2015/0057530 | A1 | 2/2015 | Roggeveen |
| 2015/0087944 | A1 | 3/2015 | Levinson |
| 2015/0208985 | A1 | 7/2015 | Huang |
| 2015/0301017 | A1 | 10/2015 | Baker |
| 2015/0338338 | A1* | 11/2015 | Messerschmidt .... A61B 5/0075 |
| | | | 435/288.7 |
| 2016/0025624 | A1 | 1/2016 | Mucci |
| 2016/0029937 | A1 | 2/2016 | Sia |
| 2016/0058354 | A1 | 3/2016 | Phan |
| 2016/0066828 | A1 | 3/2016 | Phan |
| 2016/0123869 | A1* | 5/2016 | Messerschmidt .... A61B 5/1455 |
| | | | 356/39 |
| 2016/0151569 | A1 | 6/2016 | Stafford |
| 2016/0302707 | A1 | 10/2016 | Pesach |
| 2017/0010154 | A1 | 1/2017 | Spudich |
| 2017/0082602 | A1* | 3/2017 | Pyayt ................. A61B 5/14552 |
| 2017/0127990 | A1 | 5/2017 | Levinson |
| 2017/0350814 | A1 | 12/2017 | Messerschmidt |
| 2018/0136193 | A1 | 5/2018 | Messerschmidt |

FOREIGN PATENT DOCUMENTS

| | | |
|---|---|---|
| EP | 3282937 A1 | 2/2018 |
| GB | 740181 A | 11/1955 |
| JP | 2002131319 | 5/2002 |
| WO | 1986000513 | 1/1986 |
| WO | 02058556 | 8/2002 |
| WO | 03055379 A2 | 7/2003 |
| WO | 2005080946 | 9/2005 |
| WO | 2009117416 | 9/2009 |
| WO | 2011153271 A1 | 12/2011 |
| WO | 2013058084 | 4/2013 |
| WO | 2013134786 A2 | 9/2013 |
| WO | 2013155458 A1 | 10/2013 |
| WO | 2013156806 A2 | 10/2013 |
| WO | 2013180652 A1 | 12/2013 |
| WO | 2013186628 | 12/2013 |
| WO | 2014191980 | 12/2014 |
| WO | 2015009970 A1 | 1/2015 |
| WO | 2015112919 | 7/2015 |
| WO | 2015131151 A2 | 9/2015 |
| WO | 2015166237 A1 | 11/2015 |
| WO | 2015179288 A1 | 11/2015 |
| WO | 2015179969 | 12/2015 |
| WO | 2016086071 A1 | 6/2016 |
| WO | 2016168090 A1 | 10/2016 |
| WO | 2017165403 A1 | 9/2017 |
| WO | 2018085699 A1 | 5/2018 |

OTHER PUBLICATIONS

Agamatrix, Inc., Connected Health, http://agamatrix.com/products/connected-health/.

Alam, "Measurement of pH in Whole Blood by Near-Infrared Spectroscopy", Applied Spectroscopy, Mar. 1, 1999, pp. 316-324, vol. 53, issue 3—Abstract.

Bo, "Capillary method for measuring near-infrared spectra of microlitre volume liquids", Journal of Zhejiang University-3CIENCE A, Feb. 1, 2007, pp. 171-175, vol. 8, Issue 2—Abstract.

Domjan, "Rapid Analysis of Whole Blood and Blood Serum Using near Infrared Spectroscopy", Journal of Near infrared Spectroscopy, Mar. 1, 1994, pp. 67-78, vol. 2, Issue 2—Abstract.

Eigenvector Research Incorporated website. Accessed Apr. 30, 2015. http://www.eigenvector.com/software/solo.htm.

Engel, "Seventh Sense Biosystems Sucks In $10M for Simple Blood-Draw Device", Xconomy Boston, Nov. 18, 2016, http://www.xconomy.com/boston/2016/11/18/seventh-sense-biosystems-sucks-in-10m-for-simple-blood-draw-device/#.

Gentag, NFC and Optical Skin Patches, http://gentag.com/nfc-skin-patches/.

Giardina et al., "The Multiple Functions of Hemoglobin", Critical Reviews in Biochemistry and Molecular Biology, (Mar. 1, 1995), vol. 30, pp. 165-196, XP 055498007.

Huang, "Optimal waveband and mathematical model for analysis of human whole blood glucose by near infrared transmission spectroscopy", 5th International Symposium on Advanced Optical Manufacturing and Testing Technologies, Oct. 11, 2010, Dalian, China—Abstract.

International preliminary report on patentability dated Jan. 28, 2016 for PCT Application No. US2014/047097.

International Preliminary Report on Patentability for corresponding International Application No. PCT/US2017/060007, 8 pages (dated May 16, 2019).

International search report and written opinion dated Jul. 24, 2015 for PCT/US2015/018181.

International search report and written opinion dated Nov. 6, 2014 for PCT Application No. US2014/047097.

International Search Report and Written Opinion for corresponding International Application No. PCT/US2017/060007, 10 pages (dated Apr. 5, 2018).

International Search Report and Written Opinion for International Application No. PCT/US2017/023389, 19 pages (dated Jun. 1, 2017).

Kim, "Prediction of glucose in whole blood by near-infrared spectroscopy: Influence of wavelength region, preprocessing, and hemoglobin concentration", Journal of Biomedical Optics, Jul. 1, 2006, 11(4), 041128—Abstract.

Lafrance, "Measurement of lactate in whole human blood with near-infrared transmission spectroscopy", Talanta, Jul. 4, 2003, pp. 635-641, vol. 60, Issue 4, Elsevier—Abstract.

Lakshmi et al., "A simple slide test to assess erythrocyte aggregation in acute ST-elevated myocardial infarction and acute ischemic stroke: Its prognostic significance", Journal of Pathology and Microbiology, (Jan. 1, 2011), vol. 54, pp. 63-69, XP009507350.

Liu et al. "Application of a Genetic Algorithm to Quantitative Analysis of Overlapped FTIR Spectra", Spectroscopy Letters, vol. 34, No. 1, Jan. 22, 2001.

MDPI, Diagnostics—Open Access Journal of Medical Diagnosis, https://www.mdpi.com/journal/diagnostics/.

Murayama, "Near-infrared spectroscopy for liquids of microliter voluume using capillaries with wall transmission", Analyst, 2003, Issue 7—Abstract.

Nemaura Medical, Improve blood sugar management, http://www.nemauramedical.com/sugarbeat/.

Rosenfeld, "New Skin Patch Monitors Glucose and Delivers Diabetes Drugs", Mar. 8, 2017, http://mentalfloss.com/article/93063/new-skin-patch-monitors-glucose-and-delivers-diabetes-drugs.

Staniszewska-Slezak et al. "Plasma biomarkers of pulmonary hypertension identified by Fourier transform infrared spectroscopy and principal component analysis", The Analyst, vol. 140, No. 7, Jan. 1, 2015.

Sund et al. "Cell Membrane Orientation Visualized by Polarized Total Internal Reflection by polarized total internal reflection fluorescence," Biophysical Journal, vol. 77, Issue 4, Oct. 1999, pp. 2266-2283.

Turza, "Near Infrared Analysis of Whole Blood and Plasma in Blood-Collecting Tubes", Journal of Near Infrared Spectroscopy, Jun. 1, 2006, pp. 147-153, vol. 14, issue 3—Abstract.

Wan X, "Identification of Animal Whole Blood Based on Near Infrared Transmission Spectroscopy", PubMed, Guang Pu Xue Yu Guang Pu Fen Xi. Jan. 2016; 36(1):80-3. Chinese—Abstract.

* cited by examiner

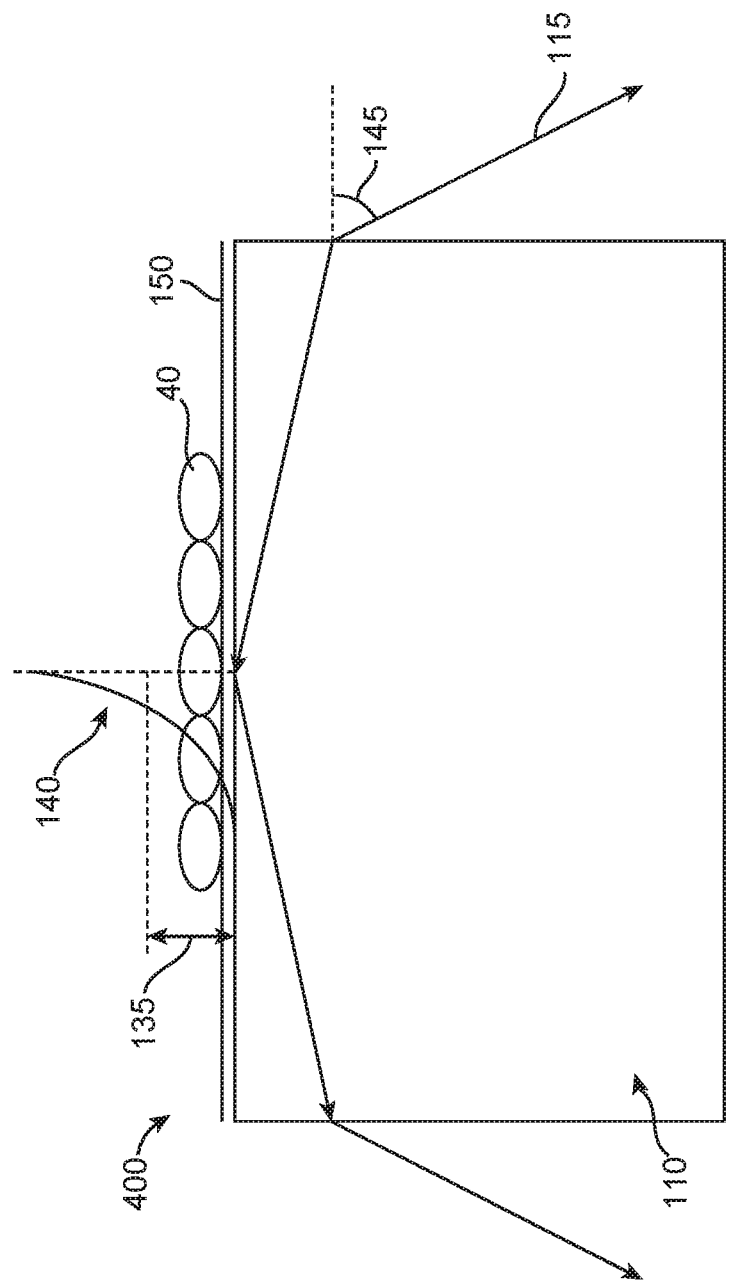

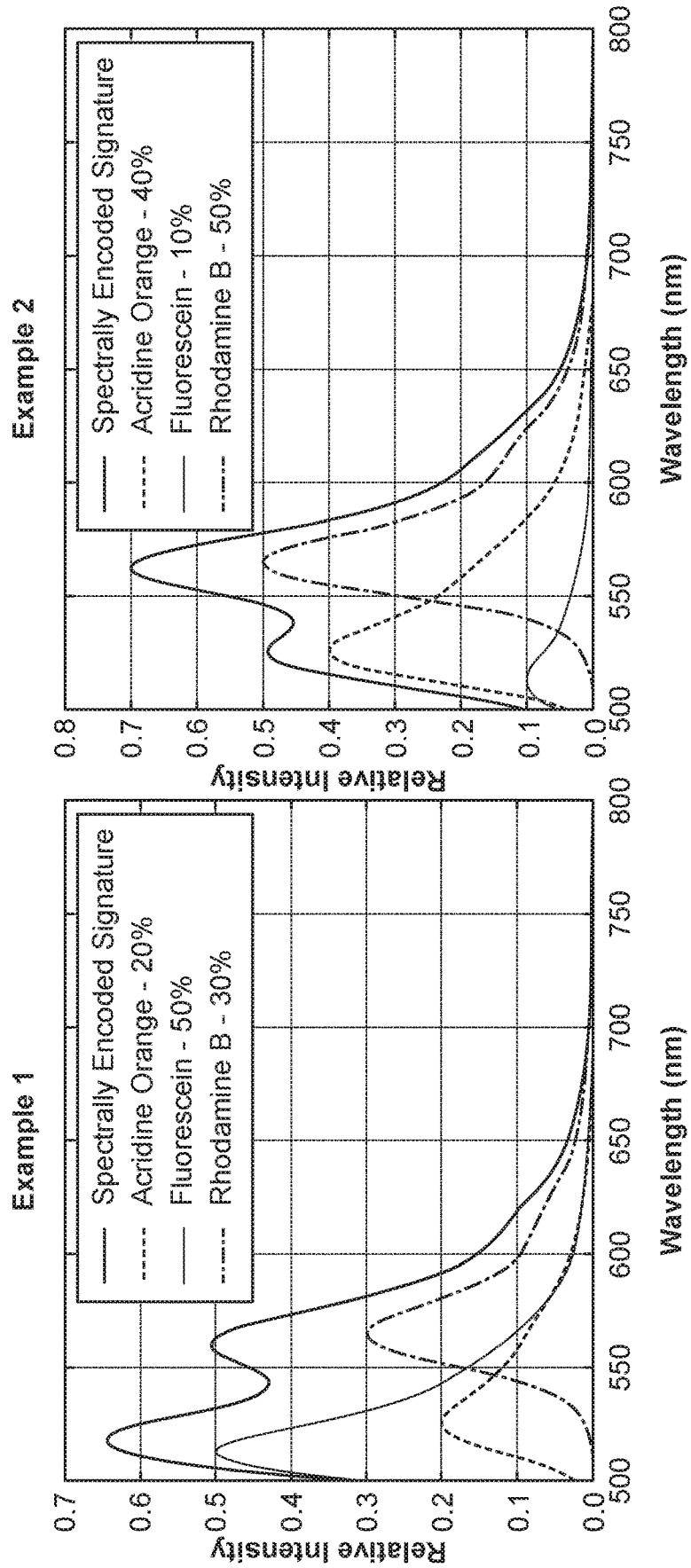

POROUS MESH SPECTROMETRY METHODS AND APPARATUS

CROSS-REFERENCE

This application is a continuation of U.S. patent application Ser. No. 16/137,012, filed Sep. 20, 2018, now U.S. Pat. No. 10,760,965 issued Sep. 1, 2020, which is a continuation of International Application No. PCT/US2017/023389, filed Mar. 21, 2017, which claims the benefit of priority to U.S. Provisional Patent Application No. 62/310,954, entitled "POROUS MESH SPECTROMETRY METHODS AND APPARATUS", filed Mar. 21, 2016, the disclosures of which are incorporated, in their entirety, by this reference.

The subject matter of the present application is related to U.S. patent application Ser. No. 14/634,238, filed Feb. 27, 2015, entitled "METHOD AND APPARATUS FOR DETERMINING MARKERS OF HEALTH BY ANALYSIS OF BLOOD", International Application No. PCT/US2014/047097, filed Jul. 17, 2014, entitled "SPECTROSCOPIC MEASUREMENTS WITH PARALLEL ARRAY DETECTOR", International Application No. PCT/US2015/018181, filed Feb. 27, 2015, entitled "METHOD AND APPARATUS FOR DETERMINING MARKERS OF HEALTH BY ANALYSIS OF BLOOD", and International Application No. PCT/US2015/062539, filed Nov. 24, 2015, entitled "SPECTRALLY ENCODED CONSUMABLE SPECTROMETER APPARATUS AND METHODS", the entire disclosures of which are incorporated herein by reference.

BACKGROUND

The field of the present invention is related to biomarkers of health, and more specifically to one or more of detecting, diagnosing, screening, tracking over time, or ruling out, one or more conditions such as high blood pressure and the harmful cardiovascular effects of high blood pressure. Examples of harmful effects of high blood pressure can include one or more of inflammation, coronary artery disease, stable plaques, unstable plaques, or other vascular factors related to the onset of heart disease and heart attack in humans.

Prior methods and apparatus of measuring biomarkers are less than ideal in at least some respects. Prior methods and apparatus of measuring blood pressure and diagnosing subjects can be less than ideal in at least some instances. Although blood pressure measurements can be used to assess the health of a subject and guide treatment, the prior methods and apparatus can be less than ideal. Blood pressure measurements based on the sphygmomanometer, also referred to as a blood pressure cuff, can have problems and deficiencies in at least some instances. For example, blood pressure cuff measurements can result in less than ideal measurements that may be related to one or more of the following: observer error; systematic intraobserver and interobserver errors; terminal digit preference, rounding to favorite digit; observer prejudice; white coat hypertension (high only in doctor's office); masked hypertension (normal in office, high at other times of day); instrument error; defective control valve; improper fit of cuff, too large or too small; inadequate length of tubing; connections not airtight; position of manometer causes reading error; placement of cuff error; diastolic dilemma (muffling of sounds can occur 10 mm before complete disappearance); two arms exhibiting different readings; deflation too rapid. These errors can lead to inaccurate blood pressure readings that may be related to improper diagnoses in at least some instances. For example, errors as large as 20 mm Hg may occur in at least some instances.

If a subject is incorrectly diagnosed as having high blood pressure when actually having low blood pressure, this person may be placed on a daily blood pressure medication. Many of these medications may have side effects, and more people than would be ideal can be subjected to the side effects of blood pressure medications. Also, blood pressure measurement errors may result in a person who actually has high blood pressure being misdiagnosed as having low blood pressure. An incorrect diagnosis for a subject with high blood pressure can result in that subject not receiving appropriate medication, such that the high blood pressure may not be untreated in at least some instances. Inappropriate management of high blood pressure can result in injury to the subject and may even be fatal in at least some instances, and it would be helpful to have fewer misdiagnoses of high blood pressure.

Work in relation to embodiments suggest that it would desirable to have a record of blood pressure and of cardiovascular health over a period of time, rather than an instantaneous measurement like brachial cuff pressure.

Although blood chemistry is the gold standard for screening, diagnosis, and therapy in health wellness and medicine, the prior methods are less than ideal in at least some respects. Currently, a blood panel is requested by a physician and the patient is instructed to travel to a blood laboratory where a phlebotomist can draw blood from the antecubital vein into a series of special collection tubes. The blood is then sent to a central blood chemistry laboratory where it is chemically analyzed using numerous wet chemical assays that have been developed and validated over the years. More recently, a small portion of these tests can be performed in a physician's office using specialized machines employing enzymatic assays. Such delivery of blood to various locations can be less than ideal.

Blood chemistry testing is rapidly moving to the point-of-care (POC) for many reasons. The biggest of these are cost and compliance. Blood testing in the POC and eventually in the home can significantly decrease healthcare costs, can be trackable and reportable, and can be immediate and actionable, sticky, and socially supportive compared to central lab testing. However, current central lab methods often do not translate to the POC and the home, since they often require complicated wet chemistry and expensive instrumentation.

In light of the above, it would be desirable to provide improved methods and apparatus for measuring biomarkers of a patient, such as biomarkers useful in determining blood pressure. Ideally such methods and apparatus would provide a more accurate reading of blood pressure with less variability and fewer false negatives and false positives for high blood pressure, provide a more accurate determination of central blood pressure, allow improved treatment and management of blood pressure, and provide an indicator of blood pressure and cardiovascular health over time.

SUMMARY

Described herein are apparatus, systems, and methods for spectroscopic analysis of samples. In many embodiments, an apparatus for providing spectroscopic analysis of a sample comprises a sample holder. For example, the sample holder may comprise a consumable single use sample holder that can be readily coupled to and removed from a measurement apparatus such as a spectrometer. The sample holder may comprise a measurement surface configured to receive the sample during measurement, wherein the measurement surface may comprise a porous mesh. The porous mesh can receive the sample to optimally configure the sample for spectroscopic measurement, as described in further detail herein. The sample disposed within the pores over the measurement surface can be measured using one or more of many optical measurement modes. Measurement signals can be transmitted to a remote server for analysis, and the analyzed spectral data can be transmitted to a personal computing device of the user.

The sample holder can be provided with one or more absorbent members to absorb excess sample placed on the measurement surface. The absorbent members having absorbed sample can be sent out to a central laboratory for further analysis. The analysis results can also be transmitted to the personal computing device of the user.

BRIEF DESCRIPTION OF THE DRAWINGS

A better understanding of the features and advantages of the present disclosure will be obtained by reference to the following detailed description that sets forth illustrative embodiments, in which the principles of the disclosure are utilized, and the accompanying drawings of which:

FIG. 10 shows light entering a germanium optical structure at an incident angle to generate an evanescent wave;

FIGS. 16A-16D show infrared absorbance spectrally encoded signatures; and

DETAILED DESCRIPTION

Although the detailed description contains many specifics, these should not be construed as limiting the scope of the disclosure but merely as illustrating different examples and aspects of the present disclosure. It should be appreciated that the scope of the disclosure includes other embodiments not discussed in detail above. For example, embodiments within the scope of the disclosure include various combinations of described features or elements not shown or described in detail. Various other modifications, changes and variations which will be apparent to those skilled in the art may be made in the arrangement, operation and details of the method and apparatus of the present disclosure provided herein without departing from the spirit and scope of the invention as described herein.

Described herein are methods and apparatus for spectroscopic analysis of samples. In many embodiments, an apparatus for providing spectroscopic analysis of a sample comprises a sample holder. For example, the sample holder may comprise a consumable single use sample holder that can be readily coupled to and removed from a measurement apparatus such as a spectrometer. The sample holder may comprise a measurement surface configured to receive the sample during measurement, wherein the measurement surface may comprise a porous mesh. The porous mesh can receive the sample to optimally configure the sample for spectroscopic measurement, as described in further detail herein.

The embodiments as disclosed herein are particularly well suited for performing spectroscopic analysis of red blood cell (RBC), proteins, lipids, and combinations thereof, for example for assessing the risk of cardiovascular diseases. Some exemplary conditions or diseases that may be assessed using the spectroscopic analyses as described herein include blood glucose level, blood pressure (e.g., average systolic blood pressure), lipid level (e.g., total cholesterol, high-density lipoprotein (HDL), low-density lipoprotein (LD), triglycerides), hemoglobin A1c level (HbA1c), hematocrit (Hb), and inflammation (e.g., plasma fibrinogen). The spectroscopic analysis can be performed without in vitro enzymatic analysis, and without lysing the cells or pretreating samples, for example.

Although specific reference is made to the measurement of blood samples, embodiments as disclosed herein will find application in many fields where spectroscopic measurement of samples may be helpful such as diabetes monitoring, epidemiology, space exploration, and spectroscopy. In particular, the embodiments disclosed herein may be well-suited for spectroscopic measurement of samples comprising cells or macromolecules.

As used herein a waveguide encompasses a light guide.

As used herein like characters identify like elements.

As used herein light encompasses electromagnetic energy having at least one wavelength within a range of the electromagnetic spectrum extending from the ultraviolet to the far infrared.

Figure 1:
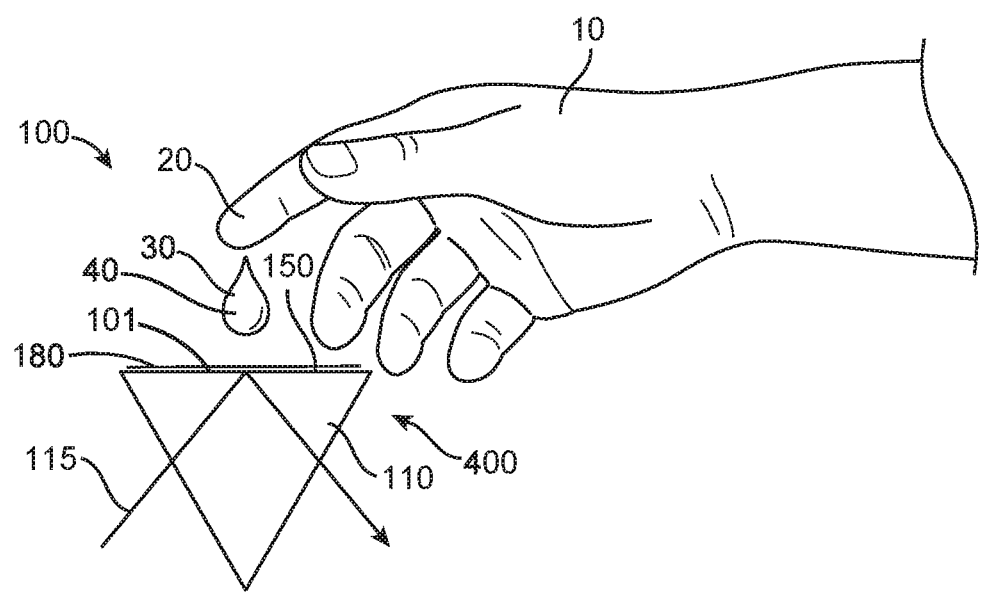
FIG. 1 shows a blood sample from a subject being placed on a measurement surface in order to measure one or more biomarkers, in accordance with embodiments.

FIG. 1 shows a blood sample 30 from a subject being placed on a measurement surface 101 of a sample holder 400 to measure the blood sample. The sample holder 400 may comprise components of a sample measurement apparatus 100 as described herein. In many embodiments, the sample holder 400 comprises a wave guide such as an attenuated total reflectance (ATR) crystal. The sample holder 400 may comprise a porous mesh 180 disposed over the measurement surface 101, such that the porous mesh receives the blood sample. Optionally, the sample holder may further comprise a spectral encoding material 150. The spectral encoding material 150 can be provided with the sample holder 400 in one or more of many ways, for example as one or more layers, a solution, particles, or a suspension of particles. Alternatively or in combination, the spectral encoding material 150 may comprise a spectral encoding structure such as a grating, a hologram, a diffractive structure in order to provide the measurement signal with spectral encoding.

The blood sample 30, comprising red blood cells 40, can be obtained from the subject. The blood sample may be obtained from a hand 10 or finger 20 of the subject, for example. Although a hand is shown the blood sample can be obtained in one or more of many known ways. The obtained blood sample can be placed on the measurement surface in one or more of many ways described herein.

The measurement surface 101 on which the blood sample is placed may comprise a surface of an optical prism 110. The optical prism may be configured to channel measurement light 115 under the blood sample, through the prism, by internal reflection. Internal reflection spectroscopy can make spectroscopic measurements at a shallow depth beyond the prism surface, since an evanescent wave is generated at that interface. This rapidly diminishing evanescent wave rapidly diminishes with distance away from the prism surface. The resulting spectrum can thereby result from only the material that is resting closest to the prism surface. In embodiments wherein the sample comprises cells, the spectrum can contain information mainly about the cell membrane and not the cytoplasm, depending on the interrogation depth of the evanescent wave as described herein. Changes in the cell membrane of red blood cells, as detected by changes in the spectra of the cell membrane, can be correlated to changes in blood pressure, for example. In many embodiments, the membrane spectrum contains spectra of one or more biomarkers having amounts corresponding to the blood pressure of the subject.

The measurement surface can be configured in one or more of many ways to measure the sample. In many embodiments, the measurement surface comprises a flat surface of an optically transmissive material such as silicon or germanium, for example. The optically transmissive material can be shaped in one or more of many ways to provide the measurement surface as described herein. For example, the optically transmissive material may comprise a prism, a flat plate, a cube, a rectangle or a Dove prism, for example. The measurement surface may comprise an ATR crystal configured to provide for multiple internal bounces of light to increase signal intensity. The ATR crystal can be configured to provide a "clean" signal, with minimal or substantially no variation of the baseline signal due to scattering effects.

Figure 2A:
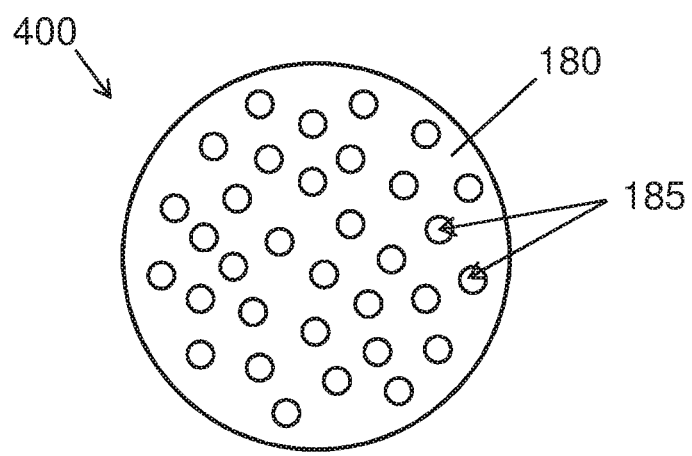
FIG. 2A shows a top view and FIG. 2B shows a side view of an exemplary sample holder comprising a porous mesh.
Figure 2B:
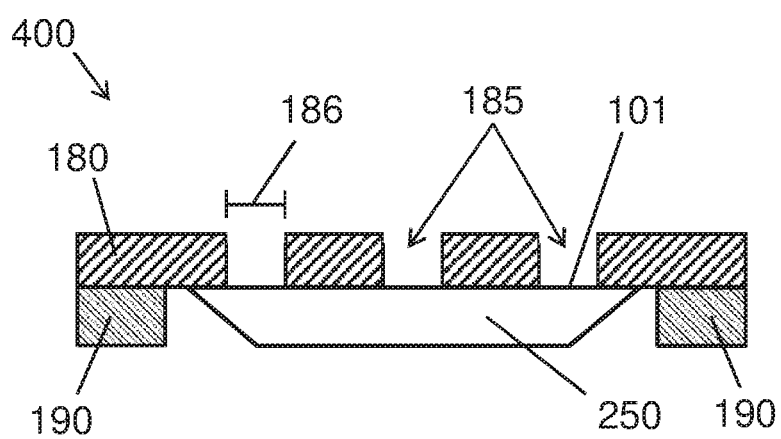

FIG. 2A shows a top view and FIG. 2B shows a side view of an exemplary sample holder 400 comprising a porous mesh 180. As shown in FIG. 2B, the porous mesh 180, comprising a plurality of pores 185, may be disposed over a measurement surface 101 such as the surface of an optical waveguide 250. The optical waveguide may comprise a silicon ATR crystal, for example. The sample holder 400 may comprise components of a sample measurement apparatus 100 as described herein. An aqueous sample for analysis may be placed over the measurement surface comprising the porous mesh, such that the sample fills the pores of the mesh. The sample disposed within a pore may be optically measured in one or more of many ways as described in further detail herein.

The plurality of pores 185 may be uniform or nonuniform in size. The pores may have an opening width or diameter 186 in a range from about 0.1 µm to about 20 µm, wherein the size of the pores may be specifically selected to accommodate the sample to be measured. For example, in embodiments wherein the apparatus 100 is used to measure red blood cells of a blood sample, a porous mesh having an average pore size of about 5 µm may be used to preferentially receive red blood cells within each pore. In embodiments wherein the apparatus is used to measure components of plasma or serum, a porous mesh having an average pore size of less than about 1 µm may be used to filter out the larger cellular components, such as red blood cells, white blood cells, and platelets.

The porous mesh may comprise a metal mesh or a porous polymeric membrane. For example, the porous mesh may comprise a silver filter membrane, a porous polyethylene (PE) membrane, or a porous polytetrafluoroethylene (PTFE) membrane. Preferably, the porous mesh produces no aberrant spectral signature in the target spectral range for sample measurement, such as in the mid-infrared spectral range (e.g., about 2 µm to about 20 µm) or the infrared spectral range (e.g., about 700 nm to about 1 mm). The porous mesh may comprise a material that is hydrophilic, to encourage spreading of a liquid sample within a pore. In many embodiments, the porous mesh can comprise a commercially available, high-purity silver filter membrane (e.g., 99.97% pure silver hydrophilic membrane filters, Sterlitech Corporation).

Optionally, the sample holder may further comprise an absorbent member 190, as shown in FIG. 2B. The absorbent member may, for example, comprise blotting paper. When the sample is placed over the measurement surface in an amount in excess of the volume capacity of the pores, the excess sample can be absorbed by the absorbent member. The absorbent member can help to ensure that a consistent amount of sample is disposed in the pores of the mesh. Further, the excess sample absorbed by the absorbent member may be used for further testing and analysis. For example, as described herein, the absorbent member having the absorbed sample may be sent to a laboratory for further analysis.

In the configuration shown in FIG. 2B, the blotting paper is arranged to be in contact with the porous mesh 180 at both the first end 183 and the second end 184 of the mesh. For example, as shown, the blotting paper can be arranged underneath the porous mesh at the first and second ends, laterally with respect to the ATR crystal 250. The sample may be deposited onto a substantially central region 181 of the porous mesh between the first end 183 and the second end 184 of the porous mesh, such that the sample spreads from the central region laterally out towards the first end and the second end. The absorbent members can remove excess sample from the first end and the second end by lateral wicking of the sample into the paper.

Figure 2C:
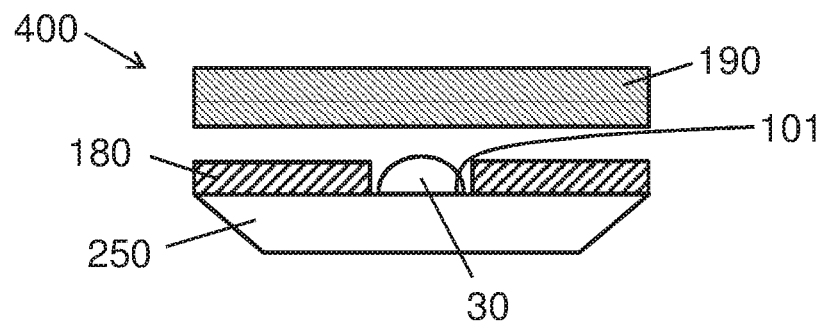
FIGS. 2C-2E show alternative configurations of the absorbent member with the sample holder shown in FIG. 2B.
Figure 2D:
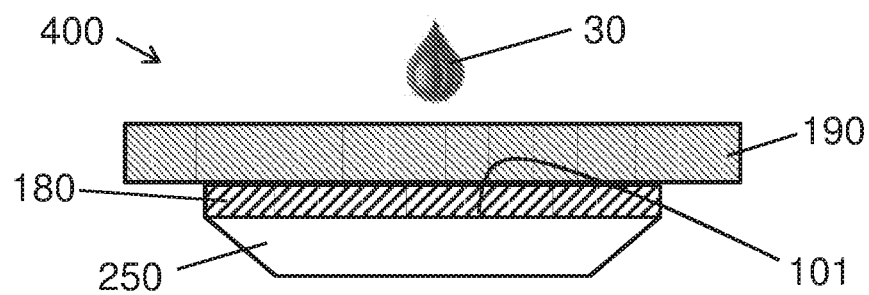
Figure 2E:
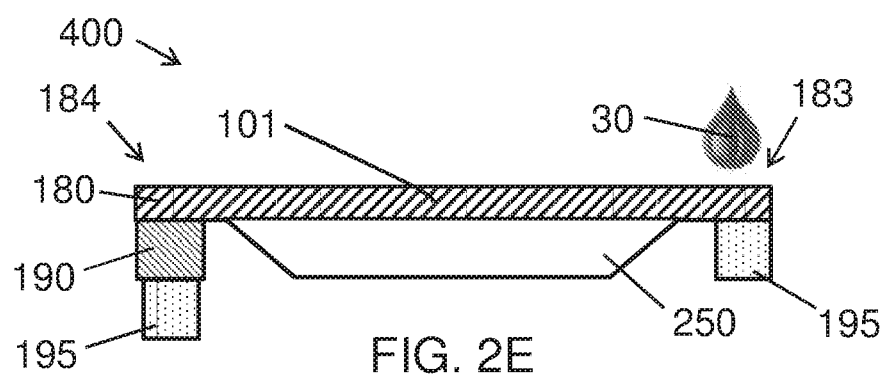

FIGS. 2C-2E show alternative configurations of the absorbent member 190 with the sample holder 400. In the configuration shown in FIG. 2C, the absorbent member 190, such as a blotting paper, is brought into direct contact with the sample 30 after the sample is placed over the measurement surface 101 and the porous mesh 180. The excess sample flowing over the upper surface of the mesh can be wicked away by the blotting paper applied from above the porous mesh and the sample. When allowing the sample to dry onto the measurement surface for dried sample measurement, the drying time may be adjusted by adjusting the thickness of the blotting paper. In the configuration shown in FIG. 2D, the absorbent member 190 is placed directly over the porous mesh 180 before the sample 30 is placed over the measurement surface 101. The sample is added to the sample holder over the blotting paper, such that the sample seeps through the blotting paper to reach the measurement surface. The measurement signal does not pick up contributions from the blotting paper (e.g., spectral signal of cellulose) since the paper is placed over the porous mesh. The combination of the blotting paper and the porous mesh can deposit a controlled amount of sample over the ATR crystal. A predetermined area may be outlined on the upper surface of the blotting paper, indicating the area of the paper that should be filled with the sample in order for a sufficient amount of sample to have been deposited over the measurement surface. A user may then add sample to the blotting paper until the outlined area is filled. In the configuration shown in FIG. 2E, the blood sample 30 is added to the porous mesh 180 at a first end 183 of the porous mesh, lateral to the ATR crystal 250. The absorbent member 190 is disposed underneath and in contact with the porous mesh at a second end 184 opposite the first end. The added sample moves laterally from the first end towards the second end as it fills the mesh, and excess sample can be absorbed by the absorbent member disposed at the second end. The sample holder 400 may further comprise a first electrical contact 195a in contact with the porous mesh at the first end and a second electrical contact 195b with the absorbent member at the second end. The two electrical contacts can be electrically coupled to an electrical instrument 360 configured to measure electric current, voltage, and/or resistance, such as a multimeter or an ohmmeter. When blood is deposited over the first end 183 of the porous mesh, the blood wets the first electrical contact 195a. The blood then traverses laterally through the porous mesh towards the second end, and wets the blotting paper sufficiently to reach the second electrical contact 195b. Electrical contact is then established between the two electrical contacts, generating an electrical resistance that may be measured with the electrical instrument. The detection of electrical resistance can provide an indication that enough blood has been added to the mesh for optical measurement. The side-filling configuration as shown in FIG. 2E can also provide gradient filtering of larger sample components such as white blood cells and red blood cells, with a higher concentration of the larger components present at the first end compared to the second end. The configuration may thus provide a way of selectively measuring certain components of the sample, wherein the sample can be measured near the first end to measure the larger components (e.g., red blood cells), and measured near the second end to measure the smaller components (e.g., plasma).

The porous mesh can provide several advantages in the optical measurement of a sample as described herein. The porous mesh can help ensure a uniform deposition of the sample over the measurement surface. A hydrophobic measurement surface, such as the surface of silicon ATR crystal, can cause a liquid sample disposed over the surface to bead and separate, making it challenging to obtain optical measurements of uniform regions of the sample. A hydrophilic porous mesh disposed over the hydrophobic measurement surface can help spread a volume of liquid evenly over the measurement surface within a pore. Also, because each pore can spread a relatively small volume of liquid sample evenly over the measurement surface, the porous mesh can reduce the volume of sample required for making the measurement. In some embodiments, the required volume of sample can as small as 1 µl or less.

The porous mesh can also help to produce consistent optical measurements of samples placed over the measurement surface. An aqueous sample may be added over the measurement surface until the pores of the porous mesh are filled. Since each pore can hold a substantially fixed volume of sample when filled, the porous mesh can help ensure that the pathlength of light travel through the sample during the optical measurement and/or the total volume seen in the optical measurement is substantially constant, thereby allowing consistent measurements to be made.

The porous mesh can also function as a size exclusion sieve to selectively separate sample components depending on the pore size, thereby enabling selective measurement of analytes of interest. For example, if the sample is a whole blood sample and the analyte of interest is a small molecule such as glucose, cholesterol, triglyceride, or other analyte present in plasma (in the nanometers in size), a porous mesh with pores that are about 1 µm or less in diameter may be used, to exclude cellular components from settling down into the pores. If the same is a whole blood sample and the analyte of interest is a red blood cell (about 4-8 µm in size), a porous mesh with pores that are no greater than about 5 µm in diameter can be used, such that red blood cells can settle down into each pore while excluding the larger white blood cells (about 10-12 µm in size). If the sample is a whole blood sample and the analyte of interest is a white blood cell, a porous mesh with pores that are at least about 10 µm in diameter can be used, to allow the white blood cells to settle down into each pore. The pore size of the porous mesh may be specifically chosen to customize the measurement apparatus for measurement of any desired analyte, some examples of which can include: cells such as red blood cells, white blood cells, and platelets; electrolytes such as $Na^+$, $K^+$, $Ca^{2+}$, $Mg^{2+}$, $Cl^-$, $HCO_3^-$, $HPO_4^{2-}$, $SO_4^{2-}$; organic nutrients such as lipids (e.g., fatty acids, cholesterol, glycerides), carbohydrates (e.g., glucose), and amino acids; organic wastes such as urea, uric acid, creatinine, bilirubin, and ammonium ions; proteins such as albumins, globulins, fibrinogen, and regulatory proteins.

Pore size may also be chosen to selectively receive or exclude sample components of specific rigidity. For example, in blood samples, blood pressure may affect red blood cell membrane rigidity, such that blood from subjects having relatively high blood pressure may comprise relatively less deformable red blood cells with relatively more rigid cell membranes, while blood from subjects having relatively low blood pressure may comprise relatively more deformable red blood cells with relatively less rigid membranes. Thus, for a pore of a given size, the more deformable red blood cells may be able to enter the pore, while the less deformable red blood cells may be excluded from the pore. A correlation between cell membrane rigidity and cell entry into pores of various sizes may be empirically derived, such that the pore size can be specifically chosen to receive only cells having a membrane rigidity below a predetermined threshold and exclude cells having a membrane rigidity above the predetermined threshold.

The porous mesh can also expedite sample drying and improve the quality of dried sample deposition. As described herein, the apparatus 100 may be used to measure dried liquid samples. The removal of water from the sample can improve the quality of the measured spectra by reducing or substantially removing interference from the water, since water can generate a significant absorption spectrum in the infrared spectral region. Reducing this interference signal can allow the optical measurement to focus on the signals generated by analytes of interest, such as various proteins or other biomarkers of the conditions being assessed (e.g., blood pressure, infections, concentration of particular molecules, etc.). The removal of water from the sample can also improve the quality of the measured spectra by concentrating the sample to yield increased signal intensity. For example, measuring a dried blood sample with an evanescence wave as described herein can result in the penetration of the evanescence wave into a plurality of cells. In this case, the red blood cell membrane may be interrogated in its entirety, and at least some of the structures or molecules within the cell may also be interrogated. An aqueous sample placed over a measurement surface comprising a porous mesh can significantly decrease drying time, since the aqueous sample disposed within a plurality of pores has a relatively larger surface area through which the sample can dry. In addition, a hydrophilic porous mesh can "wet" a relatively hydrophobic measurement surface (e.g., silicon ATR crystal surface), spreading the drops of aqueous sample placed over the measurement surface within each pore, and thereby allowing more uniform deposition of the dried sample over the measurement surface.

The volume of sample in the pore being measured may be determined in one or more of many ways. If the sample produces a strong distinct signal at a known concentration, the volume of the sample may be deduced using Beer's Law: $A = \varepsilon l c$, wherein A is the measured absorbance of the sample, $\varepsilon$ is molar absorptivity or extinction coefficient, l is the pathlength, and c is the concentration of the sample. For example, if the sample is blood, one or more native signals present in the blood, such as the Amide I or Amide II peak, can be used to deduce the volume of the measured blood. Preferably, the signal that is used for determining sample blood volume is a signal that is not affected by the subject's health or conditions. Alternatively or in combination with using native signals of the sample, an internal standard may be added to the sample at a known concentration in order to determine the volume of the measured sample. For example, a known quantity of an easy-to-measure, spectrally active material such as thiocyanate may be added to the sample. Potassium thiocyanate (KSCN) has a strong, distinctive signal in the mid-infrared spectral region that can easily be distinguished. Alternatively, the porous mesh may be impregnated with the internal standard such as KSCN, such that the aqueous sample can solvate the internal standard when deposited onto the porous mesh, to a known concentration of the internal standard in the sample. Alternatively, the internal standard may be impregnated within a sample collection device such that the aqueous sample can solvate the internal standard as it is collected in the sample collection device, to a known concentration of the internal standard in the sample. For example, a capillary tube for drawing blood (such as draw tube 440 shown in FIG. 12) may be impregnated with a known amount of KSCN, such that the blood solvates the KSCN during collection, and the blood comprising the KSCN can be subsequently deposited onto the porous mesh and the measurement surface for measurement.

Figure 3:
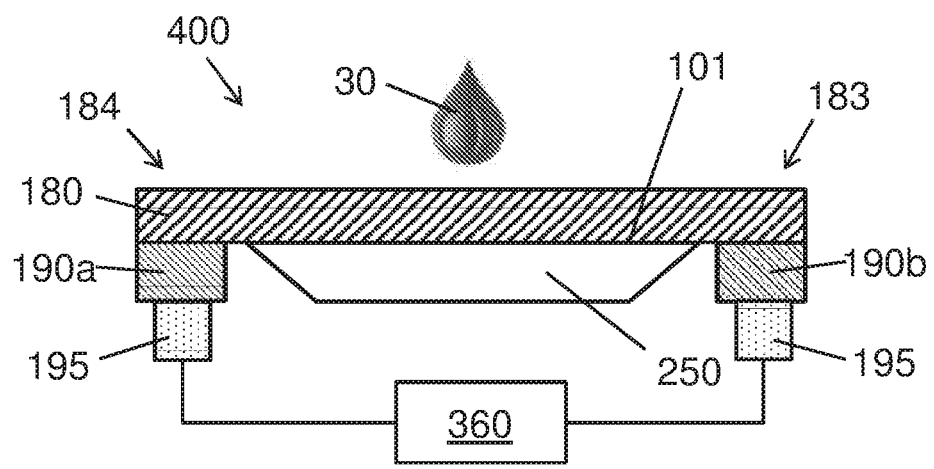
FIG. 3 shows an exemplary configuration of a sample holder for calibrating the amount of sample deposited onto the measurement surface.

The volume of sample in the pore being measure may also be determined using an electrical conductance measurement through the porous mesh as the sample is added to the measurement surface. FIG. 3 shows an exemplary configuration of a sample holder 400 for calibrating the amount of sample deposited onto the measurement surface 101. The sample holder 400 can comprise an optical waveguide 250 such as a silicon ATR crystal, and a porous mesh 180 disposed over the measurement surface 101 of the waveguide. A first absorbent member 190a may be placed underneath the porous mesh at a first side 183 lateral to the ATR crystal, and a second absorbent member 190b may be placed underneath the porous mesh at a second side 184 opposite the first side. Electrical contacts 195 can be placed in contact with each of the first and second absorbent members. The two electrical contacts can be electrically coupled to an electrical instrument 360 configured to measure electric current, voltage, and/or resistance, such as a multimeter or an ohmmeter. When enough sample is added to fill the pores of the porous mesh and wet the absorbent members (e.g., blotting paper), electrical contact can be established between the two electrical contacts, generating an electrical resistance that may be measured with the electrical instrument. The electrical instrument can be configured to emit a visual or audible alert when an electrical resistance is detected, indicating that a sufficient amount of sample has been deposited onto the measurement surface. The resistance measurement can further be used to calibrate the amount of sample added to the measurement surface, and/or the absorbent members. For example, the electrical instrument can be configured to emit a visual or audible alert when the measured resistance reaches a predetermined threshold level, indicating that a predetermined target amount of sample has been deposited onto the measurement surface and/or the absorbent members. The threshold level may be predetermined by establishing a correlation between the electrical resistance measurement and the volume of sample present on the measurement surface and/or in the absorbent members.

In many embodiments, the sample is measured near the measurement surface with total internal reflection spectroscopy (hereinafter "TIR"). With TIR, the measurement light beam is directed toward the surface at an angle so as to provide total internal reflection of the light beam from the measurement surface. Although the light beam is reflected internally from the surface, the light beam can interact with the sample on the opposite side of the surface from the light beam with an evanescent wave of the light beam. The evanescent wave of the light beam extends beyond the measurement surface by a distance related to the wavelength of the measurement light beam. In many embodiments, the evanescent wave extends beyond the surface so as to provide a penetration depth of about $0.1\lambda$ into the sample placed on the measurement surface, where $\lambda$ is the wavelength of light. The TIR light may comprise one or more of visible light, near-infrared light, mid-infrared light or far infrared light, for example. In many embodiments, the light used comprises mid-infrared light having one or more wavelengths within a range from about 2 μm (micrometer) to about 20 μm, for example. The one or more wavelengths of light may comprise a plurality of wavelengths of light to scan to a plurality of depths of the sample.

With TIR spectroscopy, the depth of the measurement is related to the measurement wavelength such that the membranes of red blood cells on or near the surface can be measured. With a 2 μm wavelength, the penetration depth can be about 0.2 μm such the penetration depth of the TIR measurement does not extend beyond a thickness of a hydrated red blood cell. With a 20 μm wavelength, the penetration depth can be about 2 μm such the penetration depth of the TIR measurement corresponds to the approximate a thickness of a hydrated red blood cell.

Figure 4:
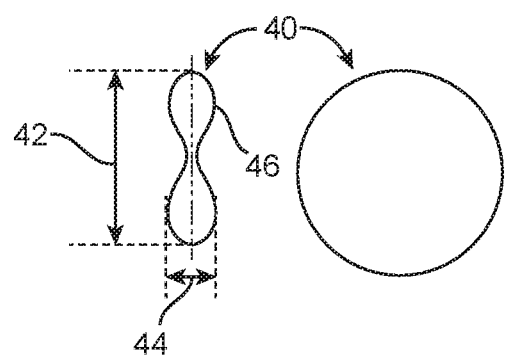
FIG. 4 shows a side profile view and corresponding dimensions of a red blood cell suitable for measurement as described herein.

FIG. 4 shows a side profile view and corresponding dimensions of a red blood cell 40 suitable for measurement as described herein. The red blood cell comprises an approximately toroidal shape having a long dimension along an elongate axis defining a length 42 of the red blood cell and a short dimension along a transverse axis defining a thickness 44 of the red blood cell. The length of the red blood cell in the fully hydrated state is approximately 7 (seven) µm and the width is approximately 2 (two) µm. As described herein, a red blood cell may also be measured in any hydration state, such as a fully hydrated state (about 60% water by weight), a fully dehydrated state (about 0% water by weight), or a partially hydrated or partially dehydrated state (between about 0 to about 60% water by weight). For an at least partially dehydrated red blood cell, the length 42 and/or the thickness 44 of the cell may be smaller than the respective dimensions of the cell in the fully hydrated state.

When the red blood cell is forced through an opening with blood pressure such as an opening of a capillary channel sized smaller than the red blood cell, the shape of the red blood cell can change to allow the red blood cell to pass, and one or more biomarkers such as ATP can be released. Alternatively or in combination, high central blood pressure can result in one or more of deformation of the red blood cell or surface changes to the red blood cell related to the high central blood pressure of the subject, and the biomarkers corresponding to these changes can be measured in accordance with embodiments disclosed herein.

In many embodiments, the methods and apparatus are configured to measure the membrane 46 of the red blood cells and identify one or more components of the red blood cells specifically. A sampling and measurement system can be configured to first separate cells from serum or plasma through sedimentation, then place a sample of blood cells onto one measuring stage and a sample of serum or plasma onto another measuring stage, for example, so as to provide separate measurements. The volume of blood sample can be small, such as a drop that could be obtained by a lancet at a finger. The stage holding the blood cells may comprise a horizontal surface on which the blood cells can be placed as described herein. The measuring stage holding the serum or plasma may comprise another measuring surface for TIR or transmission measurements as described herein, and combinations thereof, for example.

Figure 5:
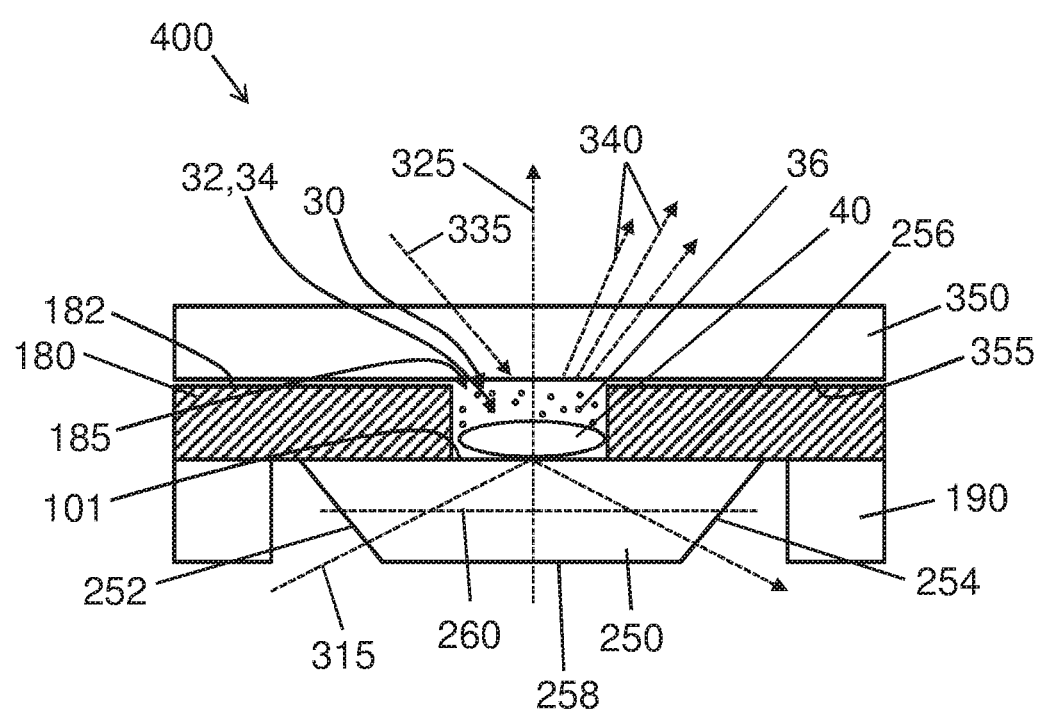
FIG. 5 shows measurement of a blood sample with a sample holder comprising a porous mesh disposed over an optical waveguide.

FIG. 5 shows measurement of a blood sample 30 with a sample holder 400 comprising a porous mesh 180 disposed over an optical waveguide 250. The sample holder 400 may comprise components of a sample measurement apparatus 100 as described herein. For example, the sample holder may comprise an absorbent member 190 and/or a spectral encoding material. The optical waveguide may comprise a dove prism as shown, or any appropriate optical structure such as a cube, rhomboid, or parallelepiped, for example. The optical waveguide may comprise an upper surface 256 comprising the measurement surface 101, and a lower surface 258 opposite the upper surface. The optical waveguide may further comprise a first end 252, a second end 254, and an elongate axis 260 extending axially through the first end and the second end and between the upper surface and the lower surface. The first end and the second end may each comprise an inclined surface.

Optionally, the sample holder may further comprise a transparent movable support 350. The transparent movable supported may be provided to shape an upper surface of the sample when placed on the sample holder 40. The transparent movable support may comprise a thickness suitable for pressurizing the sample with a pressure surface 355 for measurements as described herein. For example, the transparent movable support may be configured to pressurize the sample such that the pressure surface 355 is in contact with the upper surface 182 of the porous mesh, or such that a thin layer of sample liquid is disposed between the pressure surface 355 and the upper surface 182 of the porous mesh. Alternatively, the transparent movable support can be thin to shape the blood sample without pressurizing the blood sample, for example a microscope slide.

The blood sample 30 can be prepared in one or more of many ways for placement on the measurement surface. In some embodiments, the measurement surface, the porous mesh, and/or a solution combined with the blood sample comprises a clotting antagonist to inhibit blood clotting, in order to allow measurement of red blood cells and to separate the blood cells into a first component having a greater number of red blood cells and a second component having a greater amount of plasma as compared to the sample as drawn from the subject. Alternatively, the blood sample can be allowed to clot such that the sample comprises a first clot component and a second serum component, in which the clotting factors of the plasma have been substantially depleted to form the blood clot.

In many embodiments, the components of the serum 32 or plasma 34 and the blood cells 40, such as proteins 36, are each measured. In many embodiments, the plasma and blood cells can be separated at least partially so as to provide different measurements for each, for example separate simultaneous measurements of each.

In many embodiments, two measurement cells on two measurement stages can be used to measure the two components of blood separately, such that four measurements from four independent measurement channels or modalities can be provided. The evanescent wave measurements can be combined with the transmission measurements so as to provide four different spectral channels. Each of these channels can be interrogated with different wavelengths of light, from the visible to the far infrared region.

The blood sample may be placed over the measurement surface and measured while still in the aqueous state. Alternatively or in combination, the blood sample may be allowed to dry onto the measurement surface until a desired hydration state is reached, and the dried blood sample may be measured. The sample disposed on the measurement surface may be measured in one or more of many configurations using one or more of many measurement modalities. For example, one or more of attenuated total reflection, optical transmission, and diffuse reflection of light through or from at least a portion of the sample may be measured.

In many embodiments, the sample may be measured using mid-infrared ATR spectroscopy. For example, red blood cells disposed on the measurement surface may be measured with an evanescent wave generated from the total internal reflection of an ATR light beam 315. The ATR light beam may enter the optical waveguide through the first end 252, and exit through the second end 254 after reflecting off of the measurement surface one or more times. Preferably, the ATR light beam bounces multiples times over the length of the waveguide, thus increasing the signal intensity of light beam exiting the waveguide through the second end and detected by a detector coupled to the waveguide, as described herein. The optical waveguide can provide a first inclined surface at the first end and a second inclined surface at the second end that allow the ATR light beam 315 to be totally internally reflected and directed to the inclined surfaces at an angle that decreases reflection from the inclined surfaces. Optionally, the evanescent wave may be spectrally encoded with a spectral encoding material 150 provided with the sample holder 400.

In many embodiments, the proteins in the blood sample can begin to coat the measurement surface as time progresses. Therefore, the ATR measurement can become a way of measuring the proteins in blood with greater intensity than could be measured in the bulk serum or plasma sample. Alternatively or in combination, the red blood cells can sediment downward onto the measurement surface, and the membranes of the red blood cells within the penetration depth of the evanescent wave can be measured. The red blood cell membranes can be measured with the evanescent wave to identify, for example, high blood pressure biomarkers of the red blood cell membranes, in accordance with embodiments.

Alternatively to or in combination with total internal reflectance, the transmission of light through a thickness of the sample may be measured. For example, the transmission of mid-infrared light through a depth of an aqueous or dried blood sample may be measured. The lower surface 258 of the optical waveguide 250 may be configured to receive the transmission light beam 325, which can then be transmitted through the waveguide and the blood sample 30 disposed within a pore 185 of the porous mesh. In this measurement configuration, a spectrum representative of the bulk of the measurement cell can be obtained. For example, the transmission measurement can represent the bulk of the plasma or serum. The porous mesh can provide a fixed measurement volume of sample within each pore, such that the transmission light beam can travel over a fixed pathlength through the sample.

Alternatively to or in combination with ATR and/or transmission, the diffuse reflection of light off of the sample may be measured. For example, the diffuse reflection of mid-infrared light from the upper surface of a blood sample disposed in a pore may be measured. The diffusion reflection (DR) light beam 335 may be directed towards the sample at an angle, and the light 340 that is diffusely reflected from the sample may be measured.

The measurement apparatus comprising the sample holder can be configured in one of many ways to measure the sample using any combination of measurement modalities. For example, the apparatus may be configured to provide a combination of ATR and transmission measurements, a combination of ATR and DR measurements, or any other combination of optical measurement modalities. The sample holder may be configured in one of many ways to measure specific sample components using specific measurement modalities. For example, as described herein, the measurement surface may comprise a porous mesh of a specific pore size configured to selectively receive one or more sample components within the pores. ATR measurements can probe the sample components settled near the measurement surface within the pores, transmission measurements can probe the bulk sample composition, while DR measurements can probe the sample components near the top surface of the sample. In addition, the sample may be measured in the aqueous state and/or in the dehydrated state.

In many embodiments, the measurement apparatus can comprise two measurement cells on two measurement stages, wherein each measurement stage can measure a separate component of the sample. For example, as described herein, a blood sample may be separated into a first component having a greater number of red blood cells and a second component having a greater amount of plasma as compared to the sample as drawn from the subject. The first component may be measured on a first measurement stage, while the second component may be measured on a second measurement stage. At each measurement stage, the sample may be measured using any combination of measurement modalities as described herein. Thus, in embodiments wherein each measurement stage is configured to provide two independent measurements of the sample (e.g., ATR and DR), the apparatus can generate a total of four measurements from four independent spectral measurement channels. Each of these channels can be interrogated with the same or different wavelengths of light, from the visible to the far infrared region. In many embodiments, each of these channels can be interrogated with wavelengths of light in the mid-infrared to infrared region.

Each measurement channel may be measured as a function of time to follow changes in the sample over time. For example, a blood sample may be measured as a function of time to identify changes in blood cells and the serum and/or plasma over time. During this time, the samples can be subjected to different temperatures by embedding a heating or cooling element into the stages. Alternatively or in combination, a movable transparent support comprising an optical window can be added on top of the sample. This support comprising the window can be mounted in a frame which can create a pressure seal at the stage. In many embodiments, a high external pressure can be exerted on the sample. Pressures of up to 600 MPa can be used in order to denature and change the structure of the components and specifically proteins in the sample, for example. In many embodiments, these dynamic measurements can identify differences among biomarkers in the sample, for example differences among biomarkers of blood that have been exposed to high blood pressure versus blood from a subject without high blood pressure.

Figure 6:
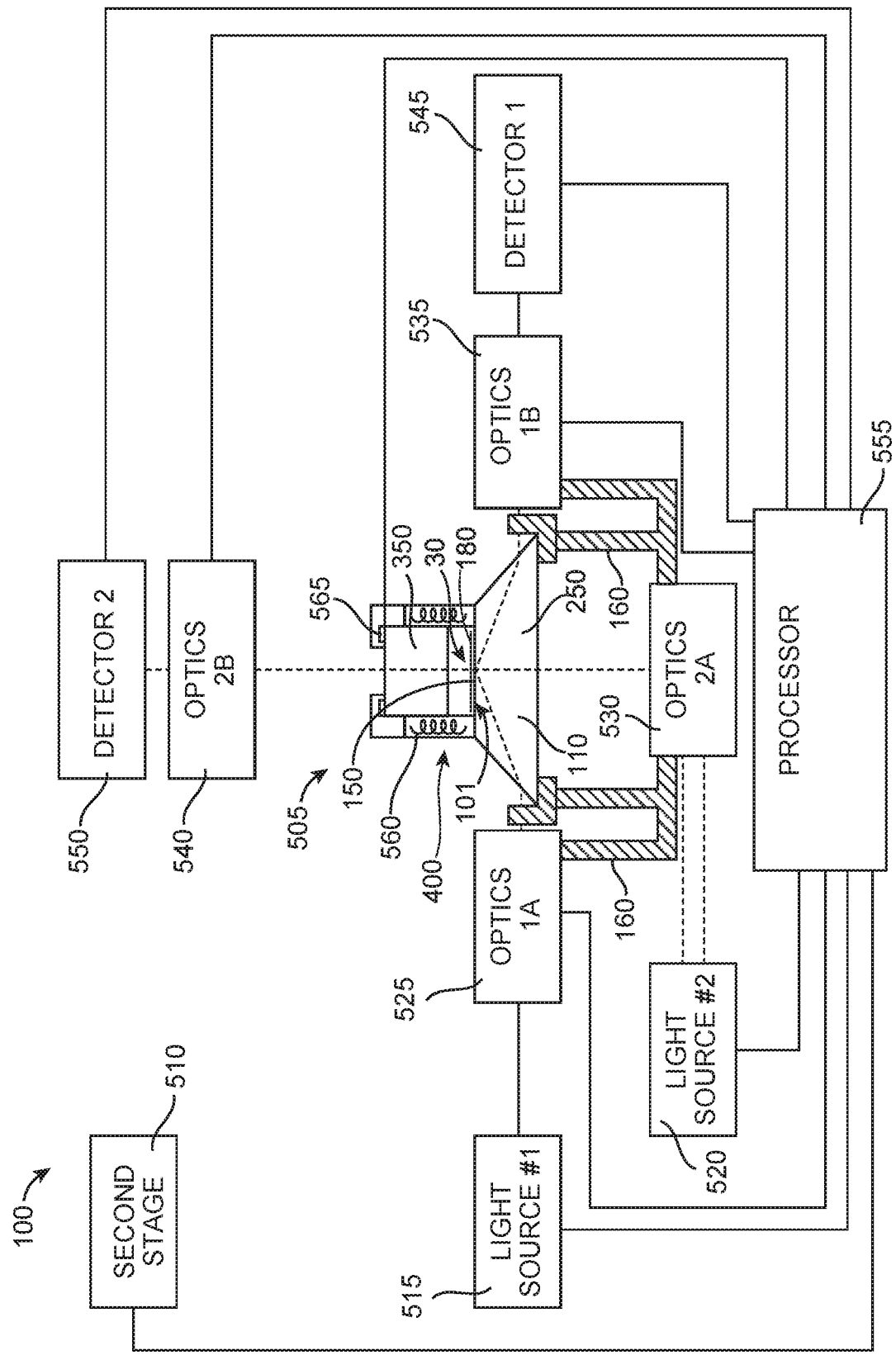
FIG. 6 shows an exemplary configuration of a measurement apparatus configured to provide ATR and transmission measurement of a sample.

FIG. 6 shows an exemplary configuration of a measurement apparatus 100 configured to provide ATR and transmission measurement of a sample. The sample may comprise a blood sample 30, for example, and the blood sample can be measured to determine markers such as blood pressure biomarkers. The apparatus may comprise one or more measurement stages, such as the first measurement stage 505 and second measurement stage 510, and corresponding optics. Each measurement stage may comprise a removable sample holder 400 comprising a measurement surface 101 with a porous mesh 180 as described herein to receive the sample. The measurement surface 101 may comprise a surface of an optical waveguide 250 such as a prism 110. The sample holder may further comprise one or more components as described herein, such as an absorbent member 190, a spectral encoding material 150, and a transparent movable support 350. The sample holder may further comprise an embedded coil 560 to heat the sample as described herein, and an actuator 565 coupled to the movable transparent support to pressurize the sample. A pressure sensor and a temperature sensor can also be provided on the measurement stage to monitor the pressure and the temperature of the sample. The prism 110 may comprise a Dove prism configured to provide the evanescent wave and bulk transmission measurements as described herein.

The removable holder 400 may comprise one of a plurality of interchangeable, single use sample holders as described herein. The removable holder 400 can be configured to engage a support 160. The support 160 may comprise a fixed support coupled to one or more optical structures and configured maintain alignment of the optics with the sample holder 400 when the sample holder 400 is placed on the support 160, as described herein.

The first measurement stage 505 and the second measurement stage 510 may be configured to receive a first sample and a second sample, respectively, as described herein. For example, the first sample may comprise a red blood cell component and the second sample may comprise a plasma component, in which the red blood cell component comprises a greater amount of red blood cells than the initial sample from the subject and the plasma component comprises a greater amount of plasma than the initial sample from the subject, for example. The first measurement stage and the second measurement stage may comprise similar components and can be coupled to light sources, optics and detectors similarly and in accordance with embodiments as described herein.

The apparatus may comprise one or more light sources, for example first light source 515 and second light source 520. The apparatus may comprise one or more input optics optically coupled to the light sources so as to receive light from the light sources, for example first input optics 525 for TIR measurements and second input optics 530 for bulk transmission measurements. The apparatus may comprise one or more output optics optically coupled to the sample holder to receive the light from the sample, for example first output optics 535 to receive the TIR light and second output optics 540 to receive the transmission light. The one or more output optics are optically coupled to one or more detectors, for example first detector 545 coupled to first output optics 535 and second detector 550 coupled to second output optics 540.

The support 160 may be coupled to the first input optics 525 and the first output optics 535 of the system in order to maintain alignment of the optics with the sample holder 400 when the sample holder 400 is placed on the support 160. The support 160 can be fixed to additional optical components of the apparatus 100 such as the second input optics 530 and the second output optics 540. The engagement structures of the support 160 and the holder 400 can be configured to place the sample holder 400 in one or more of a pre-determined position or angular orientation with respect to the optics, such that the sample of each of the plurality of sample holders can be accurately measured. The holder 400 may comprise a suitable electrical connector in embodiments comprising electrical components such as a coil 560, for example.

The components of the apparatus 100 can be coupled to a processor 555 comprising instructions to control the measurement of the sample, for example of the first sample stage. In many embodiments, the processor is configured and coupled to the one or more light sources, the input optics, the output optics and the detectors in order to measure optical spectroscopy of the sample. The processor can be coupled to the first light source to control the generation of light for TIR measurements. The processor can be coupled to the second light source to control the generation of light for the transmission measurements. The processor can be coupled to the first input optics and the first output optics to control the input and output optics of the TIR measurements as appropriate, for example when the input and output optics comprise one or more movable or electro-optical components such as shutters, gratings, etalons, mirrors, lenses, Bragg cells, prisms or wavelength selective filters, for example. The processor can be coupled to the second input optics and the second output optics to control the input and output optics of the bulk transmission measurements as appropriate, for example when the input and output optics comprise one or more movable or electro-optical components such as shutters, gratings, etalons, mirrors, lenses, Bragg cells, prisms or wavelength selective filters, for example.

The processor can be coupled to the first detector to measure the light from the TIR measurement and the second detector to measure light from the bulk transmission measurement. The detectors of the apparatus 100 such as the first detector 545 and the second detector 550 may comprise one or more of many known detectors such as a one or more of photodiode, a phototransistor, a charge coupled device (hereinafter "CCD") array, or conducting metal oxide semiconductor arrays (hereinafter "CMOS" arrays), for example. The detectors or the processor may comprise analog to digital conversion circuitry to provide a digital measurement signal to the processor.

The light sources of the apparatus 100 such as the first light source 515 and the second light source 520 may comprise one or more of many known light sources such as lamps, diodes, lasers, laser diodes, tunable lasers, optical parametric oscillators, providing a suitable wavelength of light, for example in the mid infrared as described herein. In many embodiments, one or more of the light source or the input optics is coupled to the processor to vary the wavelength of light, for example.

The apparatus 100 may comprise similar components connected to the processor for the second measurement stage. Alternatively, the first stage and the second can be interchangeable such that the first measurement stage can be removed and replaced with the second measurement stage.

The processor comprises a tangible medium to store the instructions, such as one or more of random access memory (hereinafter "RAM"), read only memory (hereinafter "ROM"), flash memory, gate array logic, a gate array, or a field programmable gate array, for example. The processor may comprise a processor system comprising a plurality of processor in communication with each other, for example. In many embodiments the processors communicate with each other with one or more known communication methods and apparatus such as wireless communication, a shared bus, a shared drive, serial communication, the Internet, and combinations thereof, for example.

Figure 7A:
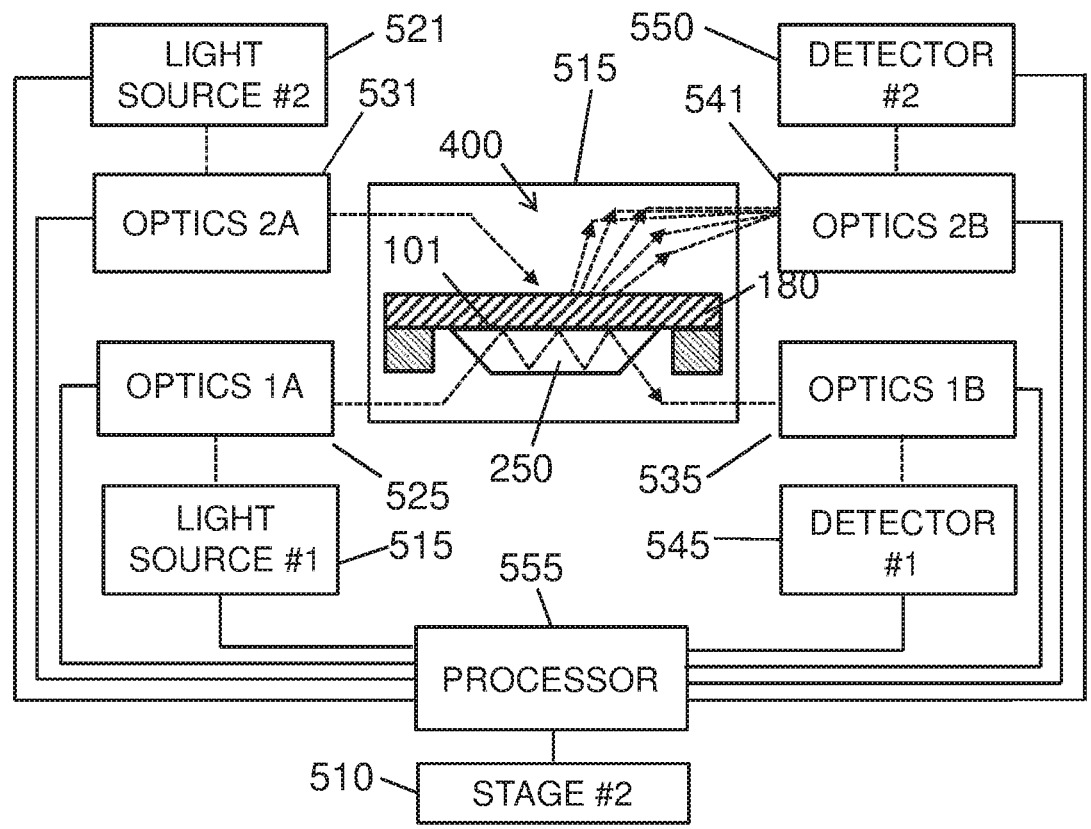
FIG. 7A shows an exemplary configuration of a measurement apparatus configured to provide ATR and diffuse reflection measurements of a sample.

FIG. 7A shows an exemplary configuration of a measurement apparatus 100 configured to provide ATR and diffuse reflection measurements of a sample such as a blood sample. The measurement apparatus may be similar in many aspects to the apparatus described in reference to FIG. 6. For example, the apparatus may comprise one or more measurement stages, such as the first measurement stage 505 and second measurement stage 510, configured to receive one or more samples or sample components as described herein. Each measurement stage may comprise a removable sample holder 400 having a measurement surface 101 with a porous mesh 180, and optionally one or more additional components as described (e.g., absorbent member 190, spectral encoding material, transparent movable support, embedded coil to heat the sample, actuator to move the movable transparent support, pressure sensor, temperature sensor, etc.). The removable sample holder 400 may be similar in many aspects to the removable sample holder described in reference to FIG. 6, and may be supported with a fixed support configured to maintain alignment of the sample holder with the optics.

The apparatus may comprise one or more light sources, for example first light source 515 and second light source 521. The apparatus may comprise one or more input optics optically coupled to the light sources so as to receive light from the light sources, for example first input optics 525 for TIR measurements and second input optics 531 for diffuse reflection measurements. The apparatus may comprise one or more output optics optically coupled to the sample holder to receive the light from the sample, for example first output optics 535 to receive the TIR light and second output optics 541 to receive the diffuse reflection light. The one or more output optics are optically coupled to one or more detectors, for example first detector 545 coupled to first output optics 535 and second detector 550 coupled to second output optics 541.

The components of the apparatus 100 can be coupled to a processor 555 comprising instructions to control the measurement of the sample, for example of the first stage and/or the second stage. In many embodiments, the processor is configured and coupled to the one or more light sources, the input optics, the output optics and the detectors in order to measure optical spectroscopy of the sample. The processor can be coupled to the first light source to control the generation of light for TIR measurements. The processor can be coupled to the second light source to control the generation of light for the diffuse reflection measurements. The processor can be coupled to the input and output optics of each stage to control the input and output optics of the TIR and/or DR measurements as appropriate, as described in reference to FIG. 6 for TIR and/or transmission measurements. The processor can be coupled to the first detector to measure the light from the TIR measurement and the second detector to measure light from the DR measurement.

Many aspects of the first and second measurement stages, first and second light sources first and second input optics, first and second output optics, first and second detector, and processor may be substantially similar to the respectively named elements described in reference to FIG. 6.

Figure 7B:
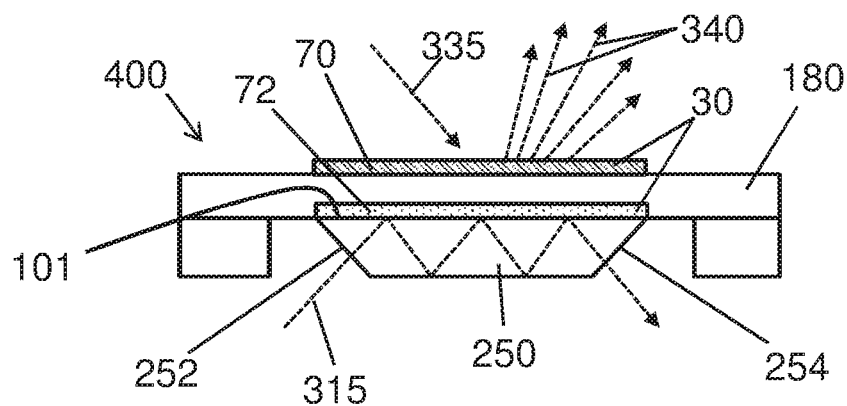
FIG. 7B schematically illustrates the measurement of a sample using the apparatus configured as shown in FIG. 7A.

FIG. 7B schematically illustrates the measurement of a sample using an apparatus 100 configured as shown in FIG. 7A. The measurement apparatus 100 is configured to provide ATR and diffuse reflection measurements of a sample such as a blood sample 30, placed on a measurement stage comprising a sample holder 400. The sample holder 400 may comprise a measurement surface 101 such as an upper surface of an optical waveguide 250. A porous mesh 180 comprising a plurality of pores may be disposed over the measurement surface to receive the blood sample, and an absorbent member 190 may be provided with the sample holder to absorb excess sample from the measurement surface. A first ATR light beam 315 may enter the waveguide through the first end 252 and travel across the length of the waveguide via total internal reflection, generating an evanescent wave at the measurement surface as described herein. The light can exit the waveguide through the second end 254, where it may be detected by a detector operably coupled to the sample holder. A second DR light beam 335 may be directed at the upper surface of the porous mesh 180, and the diffuse reflected light 340 may be detected by a detector operably coupled to the sample holder. The DR measurement may be used to identify invalid or outlier data (e.g., due to blood sampling problems), while the ATR measurement may be used to extract spectral information relating to one or more biomarkers representative of one or more conditions being evaluated (e.g., high blood pressure).

Depending on the size of the pores of the porous mesh, each measurement modality may selectively measure different components of the sample. For example, for a blood sample comprising relatively larger components (e.g., red blood cells, white blood cells, platelets) and relatively smaller components (e.g., proteins and lipids), a porous mesh with pores of a certain size can exclude one or more larger components from the pores, thus keeping those components outside of the penetration depth of the evanescent wave generated by the first light beam. Thus, the blood sample 30 can be divided into a first layer 70 and a second layer 72 on the measurement stage, wherein the first layer comprises blood components that are excluded from the pores, and the second layer comprises blood components settle down into the pores. For example, a porous mesh with pores of about 1 µm or less can exclude cells such as red blood cells or white blood cells from the pores, such that only the plasma components settle down into the pores. In this configuration, the ATR measurement can measure the plasma components, while the DR measurement can measure the cells excluded from the pores, disposed on the upper surface of the porous mesh. In another exemplary configuration, the porous mesh can have pores of about 5 µm or less, allowing red blood cells, in addition to plasma components, to settle down into the pores while excluding the larger white blood cells. In this configuration, the ATR measurement can measure the red blood cell membranes and/or plasma components, while the DR measurement can measure the white blood cells remaining on the upper surface of the porous mesh. The blood sample, or size-separated layers thereof, can be measured in their hydrated state and/or in an at least partially dehydrated state.

Figure 8:
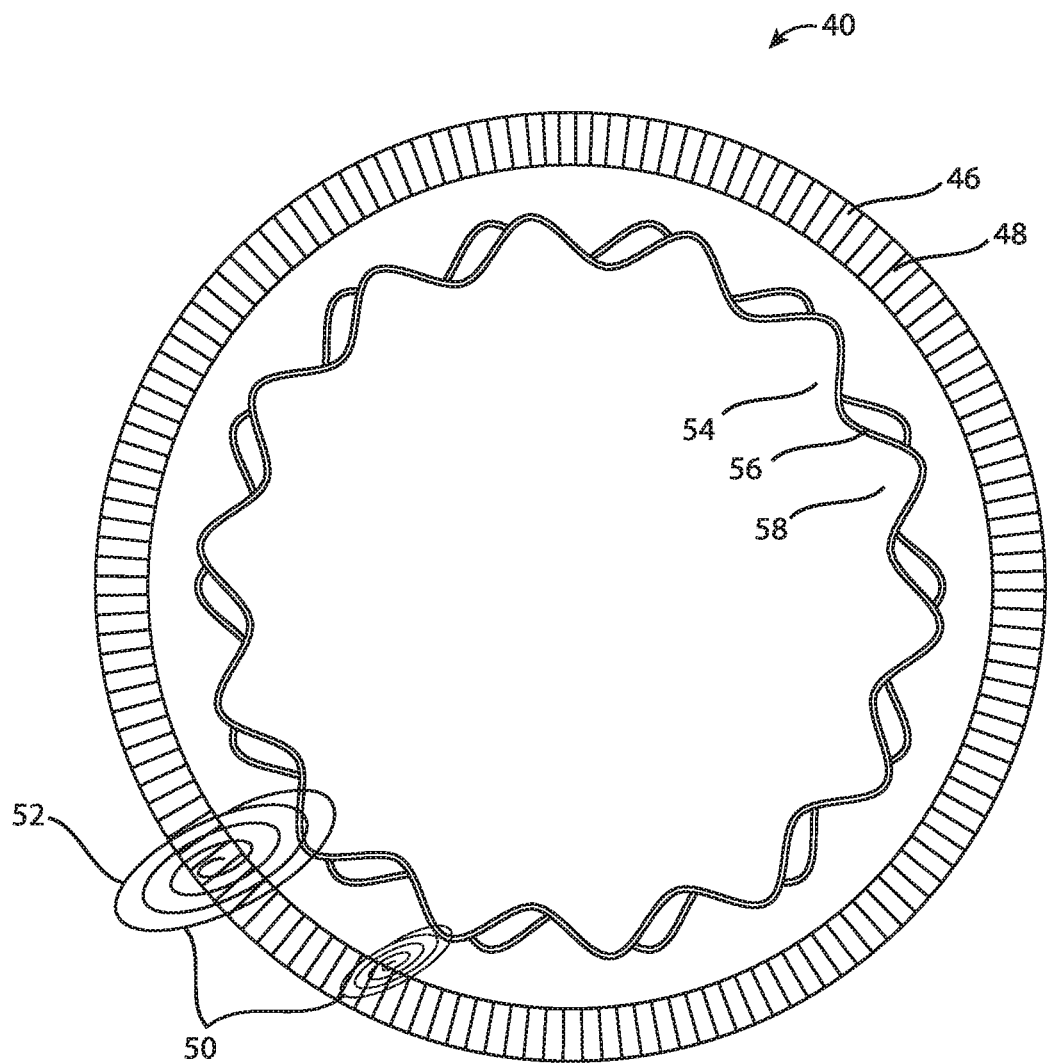
FIG. 8 shows a cross section of a red blood cell in accordance with embodiments.

FIG. 8 shows a cross section of a red blood cell 40 in accordance with embodiments. The circular cross section shows structures of the red blood cell membrane 46, trans-membrane proteins 50, and structural proteins 54 within the red blood cell. The circular cross sectional view shows the lipid bi-layer 48 of the red blood cell membrane, which may comprise a phospholipid bi-layer for example, cholesterol, and phosphatidyl choline, for example. The ratio of components of the lipid bi-layer can be measured in accordance with embodiments. The trans-membrane protein 50 may comprise one or more of many known membrane proteins, such as trans membrane proteins 52, for example. The membrane protein may comprise one or more of Band 3, Ankyrin, CD47, Rh, or Glycophorin, for example. For example, the red blood cell membrane may comprise trans-membrane protein such as Ankyrin extending through the membrane in order to transmit ions for example. The red blood cell membrane may comprise interior protein such as spectrin protein, for example a spectrin network 58 extending substantially along an interior of the cell membrane and interior to the cell wall.

In many embodiments, the red blood cell membrane corresponds to a fluid mosaic model of biological membranes, and membranes in addition or alternative to the red blood cell membrane can be measured. The membrane may comprise membrane proteins which are mobile within the phospholipid and cholesterol layer. The spectrin network of the membrane skeleton 56 provides strength to the red blood cell membrane by interacting with the other proteins of the membrane as described herein.

In accordance with embodiments, changes in the red blood cell membrane and structures associated with the red blood cell membrane can be measured. For example, lipids can be measured and changes in lipids, lipid ratios and changes in lipid ratios, proteins can be measured, protein ratios can be measured and protein to lipid ratios can be measured.

The measurement in the analysis of the red blood cell membrane can be performed in one or more of many ways, for example with one or more of principal components analysis (PCA) principle components regression (PCR), multivariate curve resolution (MCR), classical least squares (CLS), partial least squares regression (PLS), neural networks, or other bio statistical or chemometric approaches.

Figure 9:
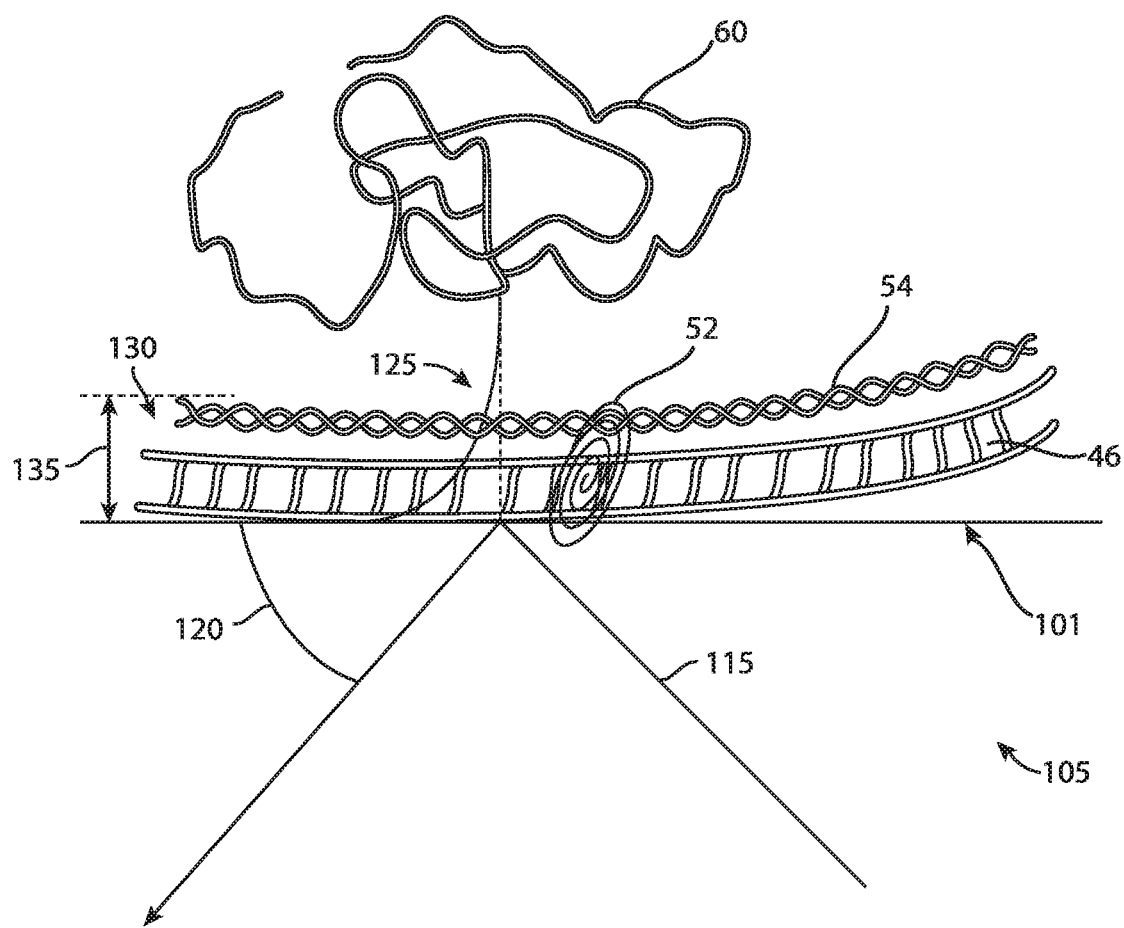
FIG. 9 shows an enlarged view of the red blood cell membrane placed on a measurement surface for measurement in accordance with embodiments.

FIG. 9 shows an enlarged view of the red blood cell membrane 46 placed on a measurement surface 101 for measurement in accordance with embodiments. The measurement surface may comprise a surface of an optical waveguide 250 as disclosed herein, and a porous mesh 180 may be disposed over the measurement surface. A measurement light beam 115 transmitted through the waveguide can generate an evanescent field 125, an evanescent vector extending at least partially beyond the upper measurement surface. A light wave is infinite on the measurement surface at an incidence angle 120 of theta. The measurement light 115 comprises a wavelength lambda. The depth 135 of the evanescent field comprises a zone of sensitivity 130. The zone of sensitivity can be adjusted based on combinations of one or more of the incidence angle Θ (theta) and the wavelength of light λ (lambda), in order to limit the depth of the zone of sensitivity of the measurement. The limitation of the measurement depth provides measurement of the cell membrane on the surface, such as the red blood cell membrane and corresponding structures such as the trans-membrane proteins 52 and the structural proteins 54, and inhibits measurement of deeper structures such as hemoglobin 60, for example. The measured structures of the membrane can be structures of the intact cell, and may comprise one or more of the trans-membrane protein Ankyrin and the structural protein Spectrin, for example. In embodiments wherein the porous mesh comprises small pores to exclude the relatively larger cellular components of blood such as red blood cells, the limitation of the measurement depth can provide selective measurement of plasma components.

The red blood cell may comprise an intact red blood cell as described herein. The zone of sensitivity can inhibit measurement of hemoglobin with a zone of sensitivity corresponding substantially to the red blood cell membrane, the lipid bi-layer of the red blood cell membrane, trans-membrane proteins of the red blood cell membrane, and structural support proteins of the red blood cell membranes, such as, spectrin for example. In many embodiments hemoglobin is positioned within the intact red blood cell at locations away from the red blood cell membrane such that the zone of sensitivity does not extend substantially into a hemoglobin molecule and, for example, does not extend across a hemoglobin molecule within the red blood cell membrane. These embodiments can provide specificity to the measurement and localization to the red blood cell membrane.

The red blood cell may comprise a substantially intact red blood cell that is at least partially dried, comprising no more than about 60% water by weight. The red blood cell may comprise a substantially intact red blood cell that is at least partially hydrated, comprising at least about 60% water by weight. The blood sample to be analyzed may comprise red blood cells of a uniform hydration state, or may comprise red blood cells of various hydration states.

In accordance with embodiments described herein, ratios of components of the red blood cell or other membranes of another cell can be measured. For example, the ratio of phosphatidyl choline to cholesterol can be measured. The ratios of phospholipids to other components can be measured such as the ratio of one or more lipid components to a ratio of one or more protein components.

The components of the red blood cell membrane can be measured in one or more of many ways, and reference is made to spectroscopy merely by way of example in accordance with embodiments.

Alternatively or in combination, rheology can be used to measure the components of the red blood cell membrane. For example, rheology measurements can be used as a reference to correlate to spectral measurements as described herein. The rheology measurement apparatus may comprise one or more capillary tubes having a diameter size to inhibit flow and limit flow and provide at least some resistance to blood flow, for example. The rheology of the plurality of red blood cells measured may correspond to structural aspects of the surface exterior, which can be affected by one or more substances on the surface of the red blood cells, for example.

The rheology components can be measured with a transform function and transfer function. For example, the flow characteristics of the red blood cells of the blood sample through capillary tubes can be measured and the impedance profiles determined for plurality of frequencies in order to determine a transform function spectra. The impedance of the blood flow through the one or more capillary tubes is measured at a plurality of frequencies in order to provide a spectrum. The mechanical spectral data can be combined with optical spectral data as described herein. Alternatively, the mechanical spectral data can be used to determine the presence of one or more biomarkers.

The rheology embodiments are well suited for combination with the optical embodiments. For example, the aggregation of red blood cells can affect the measured flow parameters of the blood, and the aggregation of the red blood cells can also be related to one or more surface components of the red blood cell membrane as described herein, for example.

In many embodiments the analysis comprises a principal component analysis (PCA), comprising the plurality of dimensions and the dimensions may comprise orthogonal eigenvectors for example. A person of ordinary skill in the art will have at least some familiarity with PCA, and can determine the presence or absence of biomarkers from a blood sample with PCA, for example.

FIG. 10 shows light 115 entering germanium optical structure 110 (index of refraction n=4) at an incident angle 145 of 80 degrees. This incident angle results in total internal reflection and a very shallow 1/e penetration depth 430 of the resulting evanescent wave 140 into the sample. The sample can comprise red blood cells 40, as shown. The ends of the germanium can be anti-reflection (AR) coated. The germanium optical structure may comprise one or more inclined prism surfaces as described herein, and may comprise waveguide as described herein, for example.

Table 1 shows penetration depths for various angles of incidence and wavelengths in different sampler surfaces (diamond, silicon, and germanium), in accordance with embodiments.

TABLE 1

Penetration Depths

| sampler surface | angle of incidence (degrees) | depth of penetration (microns) | sample index n2 | window index n1 | wavelength (microns) |
| --- | --- | --- | --- | --- | --- |
| diamond | 35 | 0.958 | 1.33 | 2.39 | 2 |
| diamond | 45 | 0.305 | 1.33 | 2.39 | 2 |
| diamond | 75 | 0.169 | 1.33 | 2.39 | 2 |
| diamond | 35 | 3.354 | 1.33 | 2.39 | 7 |

TABLE 1-continued

Penetration Depths

| sampler surface | angle of incidence (degrees) | depth of penetration (microns) | sample index n2 | window index n1 | wavelength (microns) |
|---|---|---|---|---|---|
| diamond | 45 | 1.068 | 1.33 | 2.39 | 7 |
| diamond | 75 | 0.590 | 1.33 | 2.39 | 7 |
| diamond | 35 | 4.792 | 1.33 | 2.39 | 10 |
| diamond | 45 | 1.526 | 1.33 | 2.39 | 10 |
| diamond | 75 | 0.843 | 1.33 | 2.39 | 10 |
| silicon | 35 | 0.221 | 1.33 | 3.42 | 2 |
| silicon | 45 | 0.158 | 1.33 | 3.42 | 2 |
| silicon | 75 | 0.105 | 1.33 | 3.42 | 2 |
| silicon | 35 | 0.773 | 1.33 | 3.42 | 7 |
| silicon | 45 | 0.552 | 1.33 | 3.42 | 7 |
| silicon | 75 | 0.368 | 1.33 | 3.42 | 7 |
| germanium | 35 | 0.169 | 1.33 | 4.02 | 2 |
| germanium | 45 | 0.127 | 1.33 | 4.02 | 2 |
| germanium | 75 | 0.087 | 1.33 | 4.02 | 2 |
| germanium | 35 | 0.591 | 1.33 | 4.02 | 7 |
| germanium | 45 | 0.443 | 1.33 | 4.02 | 7 |
| germanium | 75 | 0.305 | 1.33 | 4.02 | 7 |
| germanium | 35 | 0.845 | 1.33 | 4.02 | 10 |
| germanium | 45 | 0.634 | 1.33 | 4.02 | 10 |
| germanium | 75 | 0.436 | 1.33 | 4.02 | 10 |

Figure 11A:
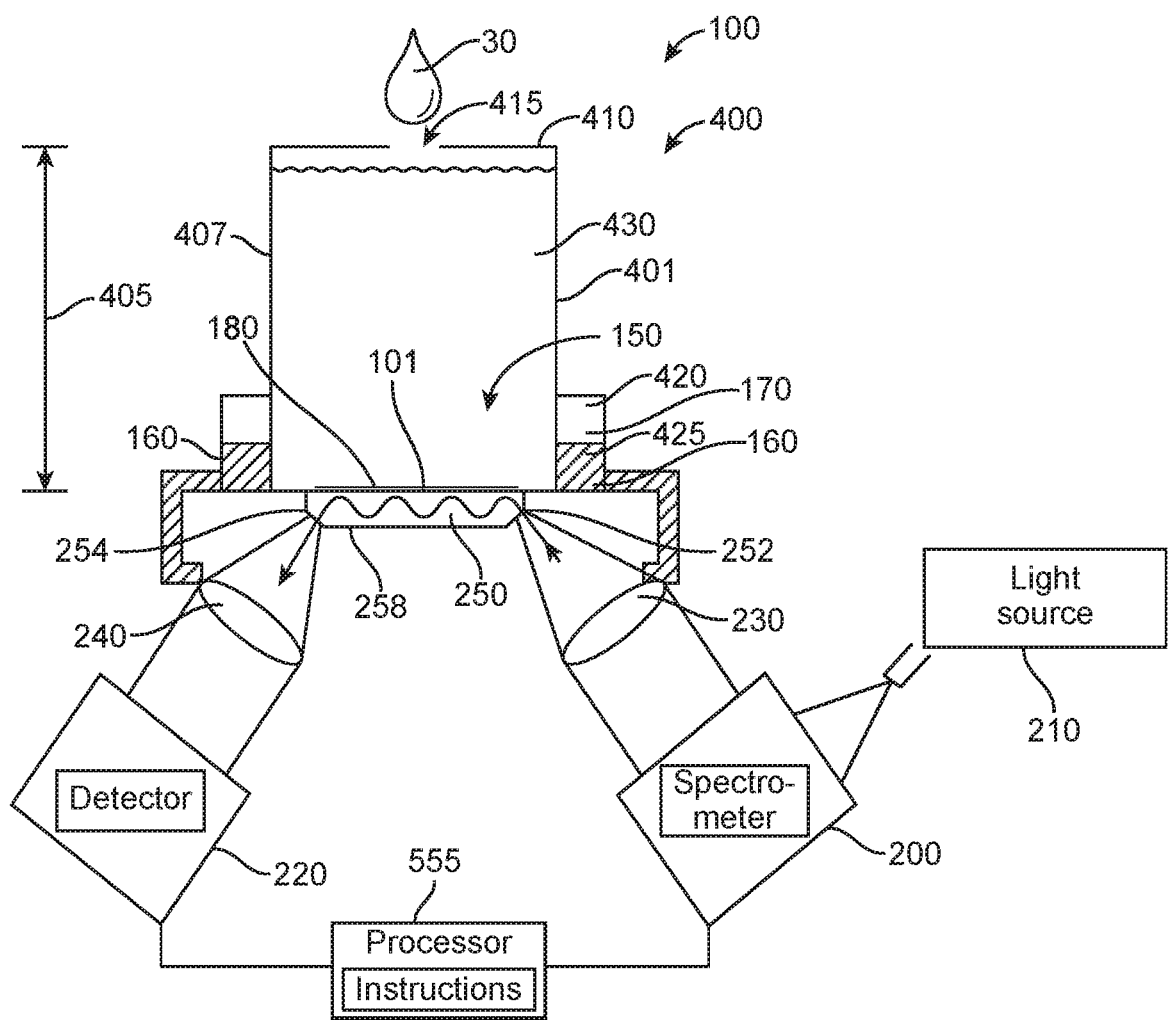
FIG. 11A shows a measurement apparatus comprising a removable sample holder and a spectrometer to measure a sample.

FIG. 11A shows a measurement apparatus 100 comprising a removable sample holder 400 and spectrometer 200 to measure a sample. The spectrometer apparatus 100 comprises one or more components as described herein, such as the processor 555 comprising instructions coupled to the detector 220 and spectrometer optics 200 comprising a light source 210. The removable sample holder may comprise a gravimetric washing container 401 to measure a blood sample 30. In many embodiments, the container 401 is coupled to a spectroscopic measurement apparatus as disclosed herein. For example, an optical waveguide 250 may be coupled to the base of the container, and a porous mesh 180 may be disposed the upper surface of the waveguide comprising the measurement surface 101. The sample 30 may be placed inside the container to deposit the sample over the measurement surface and into the pores of the porous mesh. The container can comprise a vertically extending length 405 to provide gravimetric separation. A cover or lid 410 extends over an upper portion of the container. The cover comprises an opening 415 formed in the cover.

Optionally, the removable sample holder 400 can be configured in one or more of many ways with the spectral encoding material 150 in order to encode the measurement signal of the sample. The spectral encoding material 150 may comprise a layer of material on an upper surface of the waveguide 250 as described herein, for example. Alternatively or in combination, the spectral encoding material may comprise one or more of a solution, particles, a suspension within the container, for example. The spectral encoding material may comprise a layer of material on a wall 407 of the container, for example.

The sample can be introduced into the container in many ways. For example a drop of blood 30 can be introduced into the container. Alternatively, a capillary tube comprising a blood sample can be advanced so as to extend into the opening in the cover to position at least an end of the capillary tube into the solution 430 within the container.

In many embodiments the measurement apparatus 100 comprises a support 160 fixed in relation to the spectrometer optics such that the container 401 can be placed on the support and measured with the optics aligned with the optics of the sample holder 400 as described herein. The support 160 may comprise a lower support 425 fixed in relation to the optics of the spectrometer such that the container can be placed on the lower support. The container may comprise an upper support 420 comprising an engagement structure 170 affixed to the container such that the container can be removed. The fixed lower support 425 can be sized to receive a portion of the container in order to engage the upper support engagement structure 170. The measurement apparatus comprises input coupling optics 230 such as a lens to couple to the waveguide structure of the container, and output coupling optics 240 such as lens to couple to the output of the waveguide structure to photodetectors 220.

In many embodiments, the upper support, the lower support and the coupling optics are arranged to couple the waveguide to the coupling optics when the upper support rests on the lower support. In many embodiments, the upper support comprises a lower flange or rim of the container sized and shaped to be received with the lower support and align the waveguide structure with the coupling optics when received in the lower support.

Gravimetric separation can be performed in a solution 430. The solution can be isotonic compared to blood, or can be hypertonic or hypotonic compared to blood, and combinations thereof. Hypertonic or hypotonic solution can result in conformational changes in red blood cells which may be useful for subsequent analysis. The solution can comprise saline. The solution can comprise components with known spectral bands for spectroscopic calibration, such as for example ethanol or methanol, and each spectrum can be determined in response to the known spectral bands, for example. A container, of solution can be positioned on top of a prism or other spectrometer sampling element, for example such as a waveguide as shown in FIG. 6A. The container can be shaped in one or more of many ways and may comprise a cylindrical column, for example. The container comprises a vertically extending length sufficient to allow gravimetric separation of the red blood cells from other components of the red blood cell sample such as the serum or plasma.

In many embodiments, the container column is placed on top of a waveguide structure such as prism, for example. The container may comprise a lower membrane having a thickness less than the 1/e depth of the evanescent wave in order to measure the blood sample through the membrane. The lower membrane may comprise the spectral encoding material 150. A thin optically transmissive layer of spectral encoding material 150 can be located on the upper surface of the waveguide, in which the thin material comprises a thickness less than the 1/e penetration depth of the evanescent wave, for example. The upper surface of the waveguide can be configured to receive the sample, such that the sample is placed on the layer of spectral encoding material located on the upper surface. Alternatively or in combination, the layer of spectral encoding material 150 may be located on the lower surface of the waveguide opposite the upper surface, or the surface of the waveguide configured to receive the sample.

The waveguide structure can be dimensioned in one or more of many ways as disclosed herein. In many embodiments the waveguide comprises a first end 252 to receive light energy and a second end 254 to transmit light energy. The wave guide may comprise an upper surface 256 on an upper side oriented toward the sample and a lower surface 258 on a lower side oriented away from the sample. The waveguide may comprise a thickness extending between the upper surface and the lower surface. In many embodiments the waveguide comprises a length extending in a direction of propagation from the first end to the second end. The waveguide may comprise a width transverse to the length. In many embodiments, the waveguide comprises a width greater than the thickness and a length greater than the width in order to provide a plurality of internal reflections of the measurement light energy from the upper surface of the waveguide in order to amplify the optical signal transmitted from the second end of the waveguide.

The ends of the waveguide can be configured in one or more of many ways and may comprise surfaces extending perpendicular to a long dimension of the waveguide, or inclined at an angle so as to comprise prismatic surfaces. In many embodiments, the waveguide comprises a prism, for example a dove prism as described herein.

Alternatively or in combination, the removable container 401 may comprise the waveguide structure 250. The waveguide structure can be removable with the container and located on the lower end of the container. The container can be removed or placed with the upper lid with comprising an upper hole or capillary for introducing sample into the container. A sample comprising red blood cells can be introduced to the container, and the relatively heavier red blood cells can be separated gravimetrically and settle onto the sampling surface either before or after the container has been placed on the support.

In many embodiments, the red blood cells can be washed by the solution during the gravimetric separation, such that potential contaminants can be removed from the measurement.

Figure 11B:
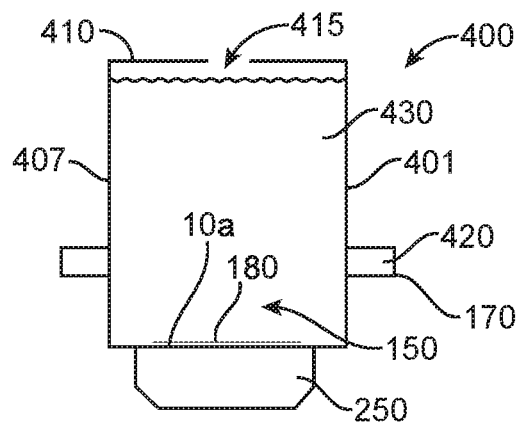
FIG. 11B shows a removable container as in FIG. 11A removed from the spectrometer.

FIG. 11B shows a removable container 401 as in FIG. 11A removed from the spectrometer. In many embodiments, the container comprises a removable container, such that the container comprises a single use consumable item and the spectrometer components can be reused. In many embodiments, the apparatus comprises a fixed support structure that engages a removable support 420 affixed to the container. The container can be accurately coupled to the spectrometer with an engagement structure 170 such as a flange, collar, or other support on the container itself. The spectrometer and associated light source and detector can be used to take measurements with the waveguide 250 on the lower end of the container.

In many embodiments the lower support 425 is fixed in relation to the optics of the spectrometer, such that placement of the container comprising the waveguide can be aligned with the measurement optics when placed in order to provide accurate spectroscopic measurements. Although the lower support 425 may be fixed in relation to the spectrometer optics, the lower support 425 and spectrometer optics can be moved together, for example when spectrometer apparatus 100 comprises a portable spectrometer. One or more of the upper support engagement structure 170 or the lower support 425 can be sized and shaped in order to position the waveguide with a position and orientation for measurement of the cells on the lower surface of the container, for example.

Additional components can also be added to the container to alter the sample if helpful. For example, gluteraldehyde can be added to the column to alter red blood cell membrane structure.

In many embodiments, a plurality of gravimetric separation containers is provided, in which each container of the plurality comprises a removable single use consumable container.

Figure 12:
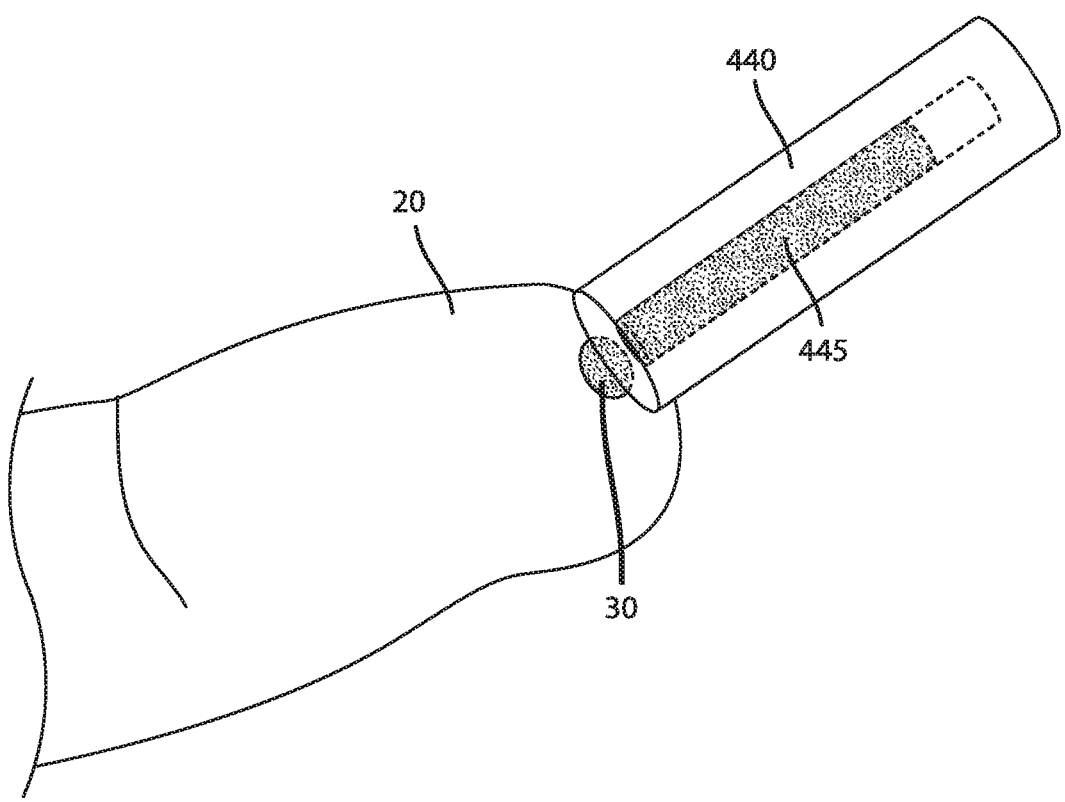
FIG. 12 shows a tube to draw a sample.

FIG. 12 shows a tube 440 to draw a sample. The draw tube can be used to draw a blood sample 30, such as a sample from a pool of blood on an external surface such as an external surface of a finger 20. In many embodiments, the draw tube comprises a permeable membrane having pores sized to wash the sample. Alternatively, the draw tube may comprise an impermeable membrane for placement of the sample in a container as described herein.

Figure 13:
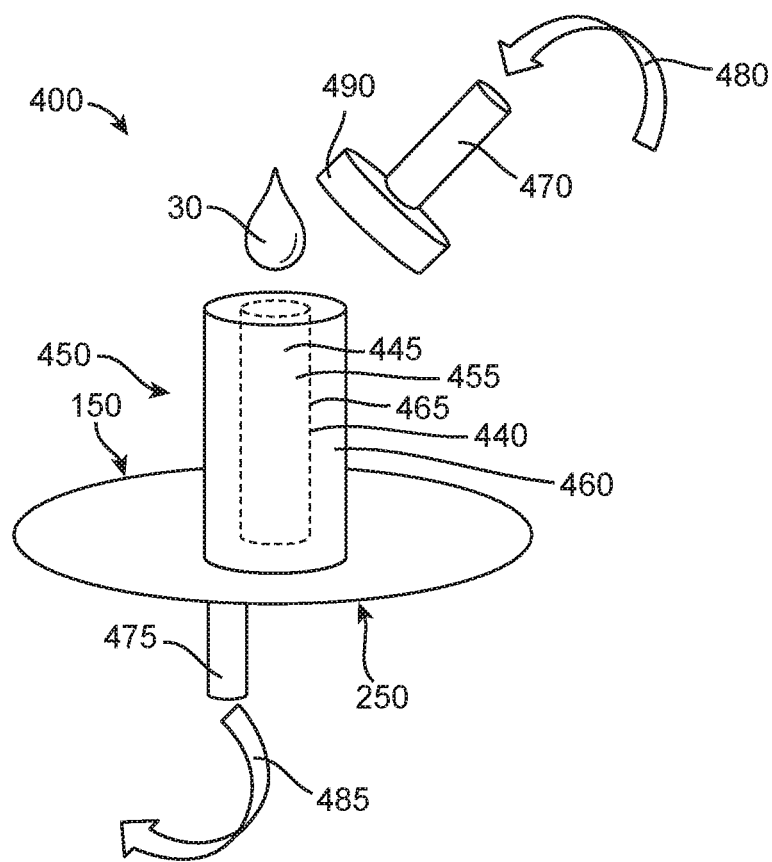
FIG. 13 shows sample delivery and cell washing with a removable sample holder as described herein.

FIG. 13 shows sample delivery and cell washing with a removable sample holder 400 as described herein. The sample holder 400 may comprise a container 450 coupled to an inlet tube 470 and an outlet tube 475. The inlet tube can provide a rinse solution 480 and the outlet tube can pass rinsate 485 from the sample container. The sample container may comprise an inner portion 455 and an outer portion 460 with the permeable membrane 465 extending therebetween, in order to provide cross-flow filtration, for example. The inlet tube can be connected to the inner portion of the sample container and the outlet tube can be connected to the outer portion of the sample container. An attenuated total reflection (ATR) waveguide crystal 250 can be located on a lower end of the sample container. The ATR crystal can comprise an upper measurement surface, over which a porous mesh may be disposed, as described herein. The cells of the sample 30 can be retained in the draw tube and deposited onto the ATR crystal for measurement as described herein. Optionally, the sample holder 400 may comprise a spectral encoding material 150, to spectrally encode the measurement signal. The rinsate column can provide the advantage of removing non-cellular material from the measured sample, such as serum or plasma and potential lysate. This rinsate may be used for other measurements that may be related to serum and plasma assays, such as cholesterol, for example.

The sample draw tube 440 comprising the semipermeable membrane 465 can be used to collect a blood sample 30, and the draw tube comprising the permeable membrane can be placed in an annular container 450 comprising a column of fluid. Alternatively, a drop of blood can be placed on an upper end of the draw tube in order to receive the blood sample with the tube. The permeable membrane may comprise an approximate pore size of about 5 µm in order to inhibit passage of cells through the pores and to allow passage of water and molecules, for example, in order to wash the sample.

A cover 490 can be placed over the annular container in order to wash the sample. The cover may comprise a tube extending from the cover. The cover may comprise an opening formed therein coupled to a lumen 445 of the tube 440 to pass fluid from the tube through the cover and into the draw tube. An outlet can be coupled to an outer annular portion of the annular container defined by the draw tube. The draw tube can be placed within the annular container such that the lumen of the draw tube defines a first inner portion of the annular container within the draw tube and a second outer annular portion of the annular container outside the draw tube.

The outlet tube can be connected to a lower portion of the outer portion of the container as shown. Alternatively, the outlet tube can be coupled to an upper portion of the sample container, and may be integrated with the cover, for example, such that both the inlet tube and the outlet tube extend from the cover.

The ATR waveguide crystal as described herein can be located on a lower end of the annular container, and coupled to spectrometer optics, such that the sample container comprises a removable sample container among a plurality of sample containers as described herein. The waveguide can be located on a lower end of the draw tube, for example.

The sample holder 400 comprising the container can provide a disposable means for washing the serum or plasma and potential lysate from the cell membranes and packing the cells onto the ATR crystal. The sample container can be used with one or more of the following steps: washing of serum or plasma and potential lysed material into rinsate column; draining a the rinsate column and a majority of the membrane straw, leaving a layer of cells on ATR crystal; and beginning spectroscopic measurement when sufficient cell membrane signal exists.

In many embodiments, spectra can be measured from the sample and statistical analysis methods can be used to generate a plurality of factors. The plurality of factors may comprise a plurality of functions upon which the data can be projected in order to determine the amount, or concentration, of each function in the sample. The factors can be orthogonal or non-orthogonal, for example. The analysis can comprise one or more of principle components analysis (PCA), principle components regression (PCR), classical least squares (CLS), multivariate curve resolution (MCR), partial least squares regression (PLS), neural networks, or other biostatistical or chemometric approaches, for example. In many embodiments, the factors are orthogonal to each other. Alternatively, at least some of the factors may comprise non-orthogonal factors. One or more relevant factors can be identified, and the red blood cell status or history can be determined in response to the one or more relevant factors. In many embodiments, the history of the red blood cells comprises a control of the red blood cells of the subject, for example a control of a condition such as high blood pressure of the subject. The one or more relevant factors may comprise one or more statistically relevant factors, for example.

In many embodiments, a plurality of spectral bands comprise peaks related to structure of the cell such as protein structure of the red blood cell. The Amide I band of frequencies comprising the Amide I peak may correspond to alpha helix protein structures of the proteins of the red blood cell membrane. The Amide II band of frequencies comprising the Amide II peak may correspond to beta-sheet protein structures of the cell membrane. The band of frequencies comprising the Amide III band may correspond to disordered protein structures of the cell membrane. The determination of factors corresponding to these spectral bands and the shifts of peaks and intensities of these spectral bands in response to the measure spectra can be used to determine the one or more biomarkers of the cellular membrane such as the red blood cell membrane.

In many embodiments, deformation of the red blood cell membrane results in measurable spectroscopic changes to the red blood cell membrane that can be measured as described herein. The measurable changes may comprise shifts in the spectral peaks as disclosed herein. The spectroscopic changes to the red blood cell membrane can be substantially instantaneous, for example upon deformation of the red blood cell membrane. Alternatively, the spectroscopic changes to the red blood cell membrane may comprise changes occurring over the history of the red blood cell, for example over a long term three month history corresponding to the 90 to 120 day functional lifetime of the red blood cell.

In many embodiments the factors can be used to determine the history of the red blood cell, and can be used to determine the long term control of a condition such as hypertension, for example. The long term control may comprise a conformational change to the red blood cell membrane that can be determined with at least one factor as disclosed herein, for example with a relationship among factors as disclosed herein.

In many embodiments, the biomarker amplifies an optical spectral signal. The biomarker may comprise a change to cell membrane, such as a conformational change to a protein of a red blood cell membrane or a ratio of components of the red blood cell membrane as disclosed herein, for example. As the red blood cells comprise a long dimension that can extend along the measurement surface and optically couple the red blood cell membrane to the evanescent wave measurement surface, the measured signal can be amplified substantially. In many embodiments, a substance related to the health status of the subject may not itself be detectable with the spectral measurements. The measurement of the red blood cell membrane can provide, however, an optical spectral signal to determine the presence of the substance. For example, spectral changes of the red blood cell membrane provided with aspirin as disclosed herein can be used to identify a response of the red blood cell membrane to aspirin, even though the presence of aspirin itself may not be detectable spectroscopically in some embodiments. The optical waveguide can be configured to provide a plurality of reflections from the evanescent wave measurement surface in order to provide an increased amplification of the measured evanescent wave signal.

Figure 14:
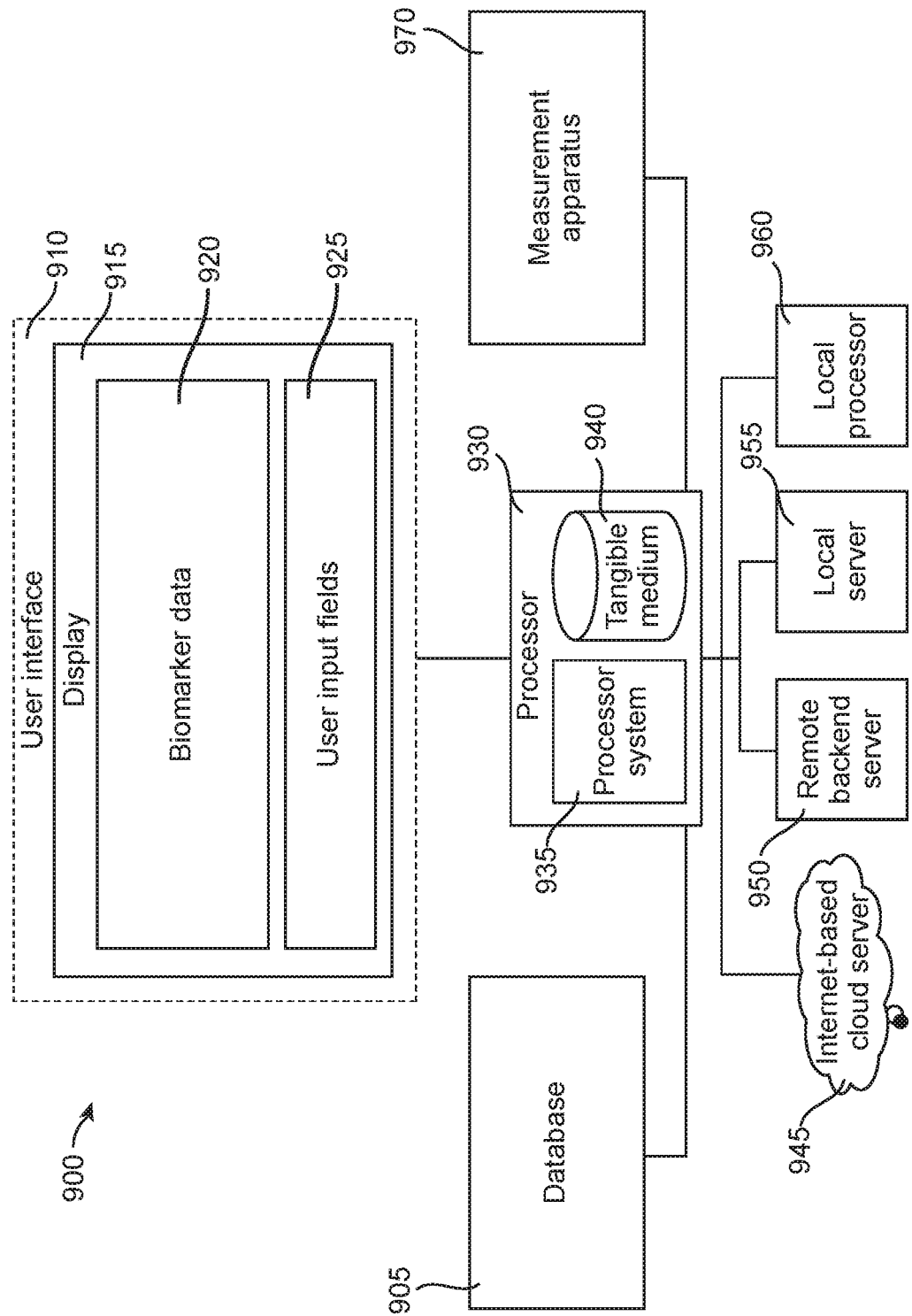
FIG. 14 shows an apparatus comprising a database and a user interface to determine identify markers of red blood cells related to health in accordance with embodiments.

FIG. 14 shows an apparatus 900 comprising a database 905 and a user interface 910 to determine identify markers of red blood cells related to health in accordance with embodiments. The apparatus 900 may optionally comprise one or more components of the measurement apparatus 970 as disclosed herein, such apparatus 500, for example. The user interface comprises a display 915 connected to a processor 930 such that the user can view the biomarker data 920 on the display. The user interface also comprises one or more user input fields 925. The processor may comprise a processor system 935 and can store data of the database for the user to see information of the database on the display. The processor comprises a tangible medium 940 storing instructions of the database, such that the user can see the information on the display. The tangible medium may comprise a computer readable medium having one or more of many known forms such as random access memory (RAM), read only memory (ROM), compact disc CD-ROM, flash RAM. The processor may comprise one or more of a plurality of Internet based cloud servers 945, a remote back end server 950, or a local server 955, or a local processor 960 for example. The display may comprise a display of a hand held processor such as a smart phone in communication with a server, for example. Each of the components of the apparatus 900 can be connected in one or more of many ways as will be apparent to a person of ordinary skill in the art, and each of the components as shown can be connected to another component, either directly or indirectly through other components and communication pathways as disclosed herein.

The measurement apparatus as described herein can be combined with the database and user interface in many ways. In many embodiments, data from the measurement apparatus is shown on the display. The data shown on the display may comprise data of the amplified red blood cell measurement signal as described herein. In many embodiments, output of the processor system, can be shown on the display, in accordance with steps of one or more methods as described herein, and the one or more processors may comprise instructions to perform the one or more method steps and output the data on the display. In many embodiments, the data output to the user interface comprises cell membrane amplification data as described herein, such as data of a plurality of cell membranes shown on the display. The data of the plurality of cell membranes may comprise evanescent wave data of a plurality of intact red blood cell membranes, for example. In many embodiments, amplified data comprises amplified cell membrane data of a plurality of washed cells, such as gravimetrically separated washed red blood cells as described herein. The data shown on the display to the user may comprise one or more biomarkers of health from the gravimetrically separated and washed membranes of intact red blood cells, for example. The one or more processors as described herein can be configured with instructions stored on a tangible medium such as a computer readable medium to provide the data on the display.

Figure 15:
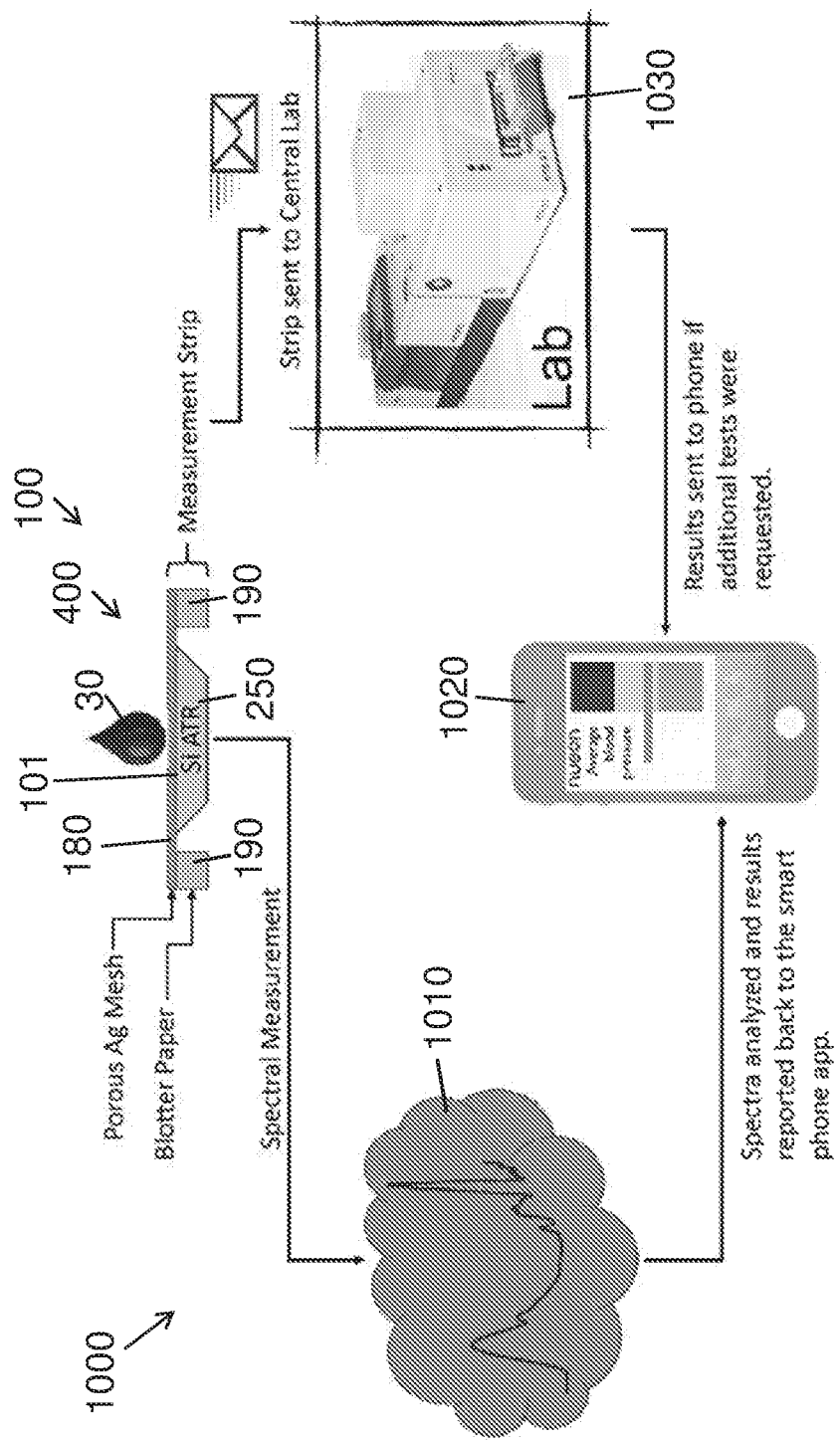
FIG. 15 shows a system for optical measurement and evaluation of a sample in accordance with embodiments.

FIG. 15 shows a system 1000 for optical measurement and evaluation of a sample in accordance with embodiments. The system 1000 comprises a spectroscopic measurement apparatus 100 as described herein, the apparatus comprising a sample holder 400 operably coupled to a spectrometer as described herein. The sample holder can comprise a porous mesh 180 disposed over a measurement surface 101 of an optical waveguide 250, and one or more absorbent members 190 in contact with the porous mesh. A user may deposit a sample 30 over the measurement surface and porous mesh for optical measurement using any measurement mode as described herein. The spectral measurement can be transmitted to a remote server, such as a cloud-based server, for analysis. The results of spectral analysis can be transmitted to a personal computing device 1020 such as a smartphone or a tablet for access by the user. The personal computing device may be configured to provide a user interface (e.g., web-based interface, mobile app, etc.), through which the user may view the results of the measurement such the average blood pressure of the subject whose sample was measured. Data may be transmitted between the measurement apparatus or personal computing device and the remote server via any suitable means, such as a data network or an Internet-based network.

When the user deposits the sample over the measurement surface, excess sample can be absorbed by the absorbent members (such as blotting paper). The absorbent members comprising the absorbed sample, or "sample strips", can be sent to a central laboratory 1030 (e.g., via mail) for further analysis. For example, the dried sample present on a blotting paper strip can be analyzed via an enzyme-linked immunosorbent assay (ELISA) to measure the concentration of one or more analytes (e.g., total cholesterol, high density lipoprotein (HDL), low density lipoprotein (LDL), triglycerides, etc.). Since the blotting paper can hold a known volume of the sample, a portion of the paper of a specific size can be punched out to test a known total volume of the sample, such that quantitative analysis results can be produced. The results of the further analysis conducted with the sample strips can be transmitted to the personal computing device 1020 of the user, for example via a wireless network.

To facilitate tracking and identification of the sample strips, the sample strips may be provided with unique identifiers, such as barcodes or serial numbers attached to the absorbent members. The unique identifiers may be read at either the user's location or the central laboratory, or at both locations to ensure a match. The unique identifiers may be read using any appropriate means for the type of unique identifier. For example, a barcode identifier may be scanned using a barcode reader, or a serial number may be imaged using a camera and text recognition of the image performed to read the serial number. Optionally, the sample spot on the sample strip may be imaged at either or both of the user's location and the central laboratory for quality verification. It may also be possible to automatically detect the identity of the subject whose sample is present on the sample strip via biometric detection. For example, a blood sample may produce a distinct spectral signature for each individual, and the identity of the subject may be recognized based on the spectral signature. Alternatively or in combination with other identification means, the sample strips may be identified using spectrally encoded signatures. Each absorbent member or strip may be encoded with a distinct spectral signature that may be identified via spectral measurement. For example, each absorbent member or strip may comprise one or more spectral encoding materials with spectrally encoded signatures, as shown and described in reference to FIGS. 16A-16D. The spectral encoding materials may comprise polymers, coatings, paints, fibers, dyes, pigments, or other materials known to have distinct spectral signatures.

FIGS. 16A and 16B show spectrally encoded signatures for first and second fluorescent material combinations. Two different examples using fluorescence spectroscopy in which the underlying fluorophore emissions dictate the overall spectrally encoded signature. Although only two signatures are shown, thousands of signatures, or more, can be produced using three fluorophores, for example. Even more signatures can be produced using more fluorophores, in accordance with embodiments.

Figures 16C, 16D:
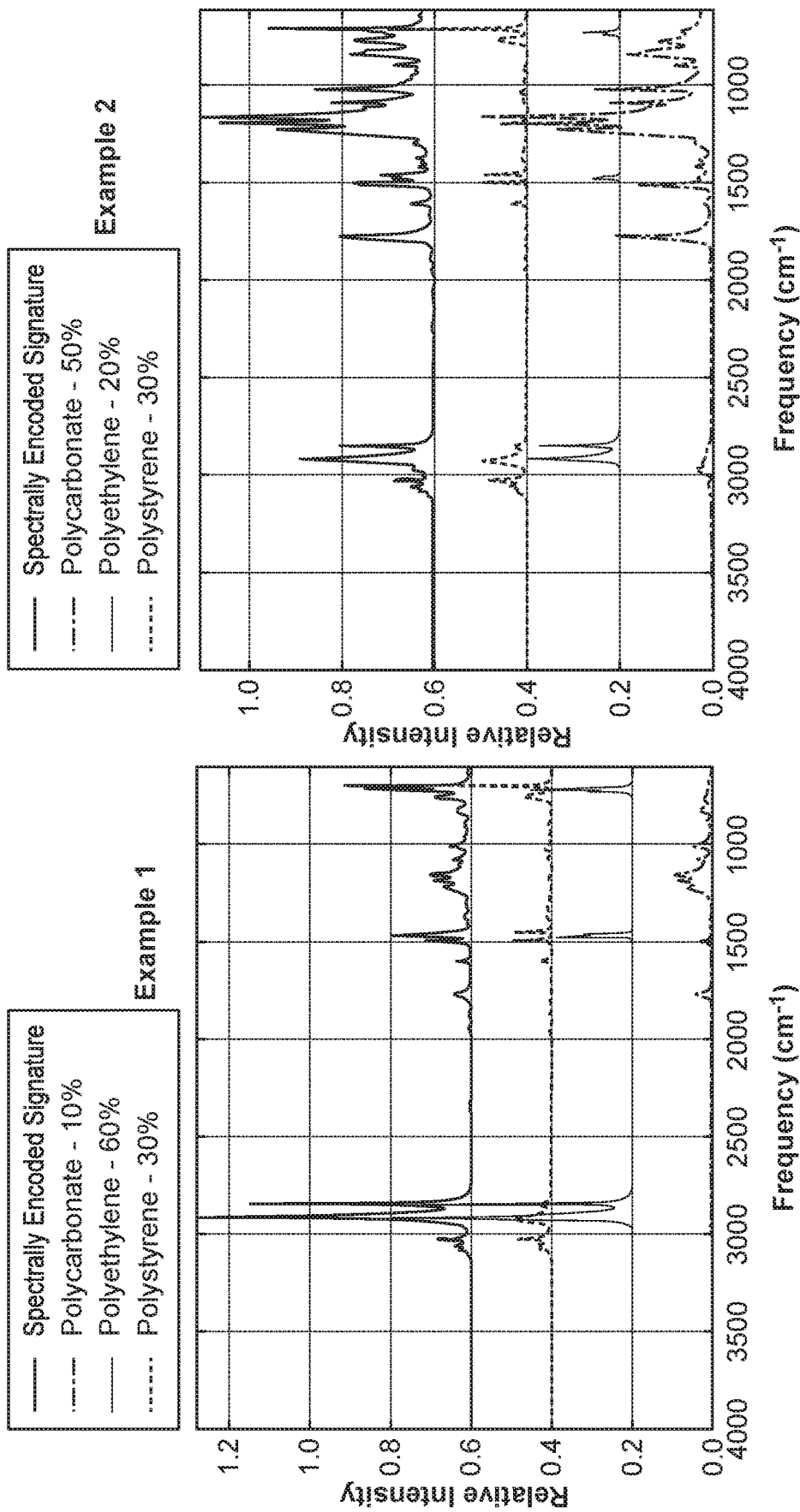

FIGS. 16C and 16D show infrared absorbance spectrally encoded signatures. The spectra have been offset to show the spectral features of the individual components and the composite spectrally encoded signature. The spectra show two different examples using infrared spectroscopy in which the underlying absorbance of each polymer material provides the overall Spectrally Encoded Signature. Although only two unique encoded signatures are shown, thousands of signatures can be produced with different intensity combinations of the polymers as described herein. Even more signatures can be produced by increasing the number of polymers.

Figure 17:
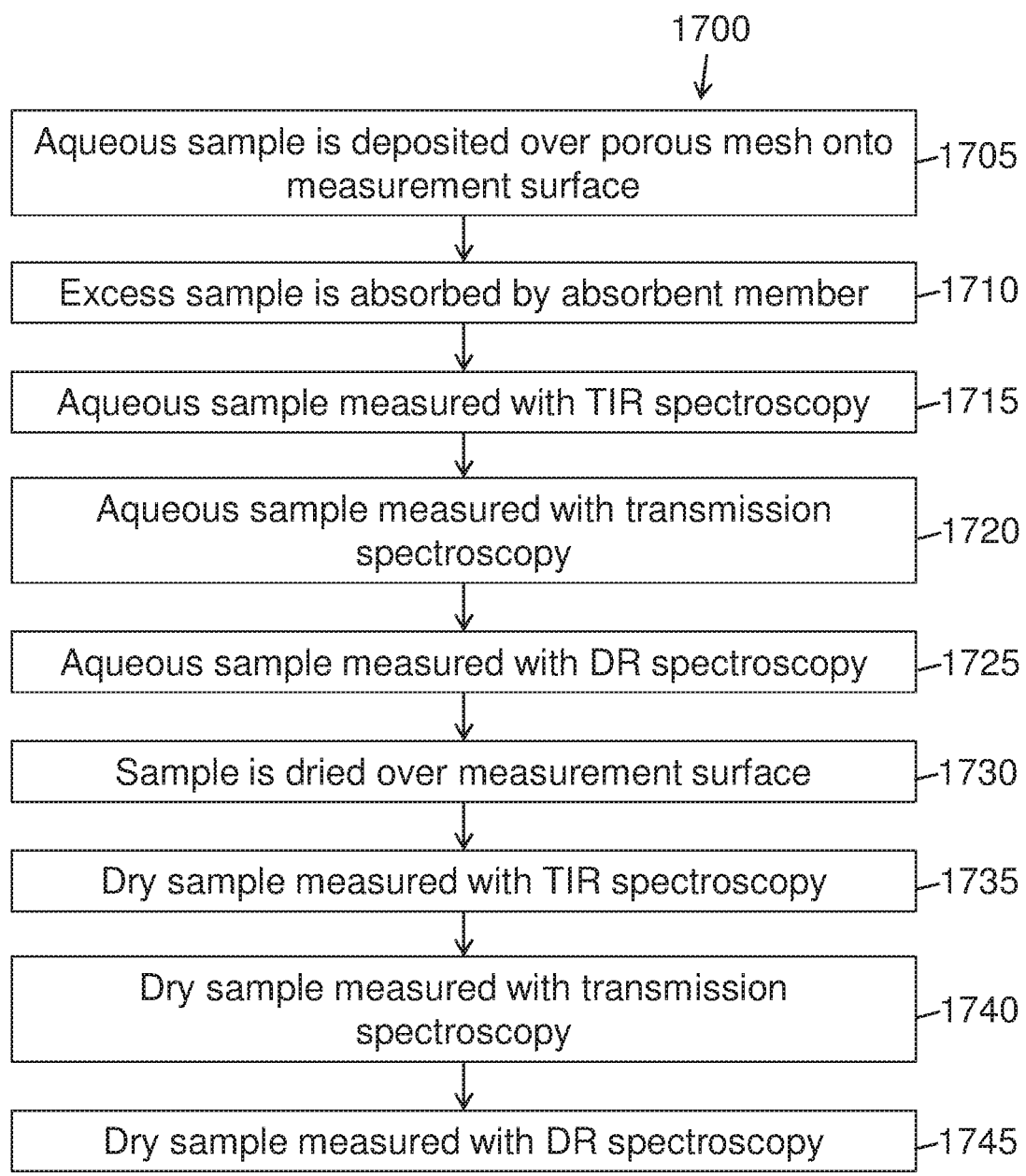
FIG. 17 shows a method of measuring a sample in accordance with embodiments.
Figure 17:
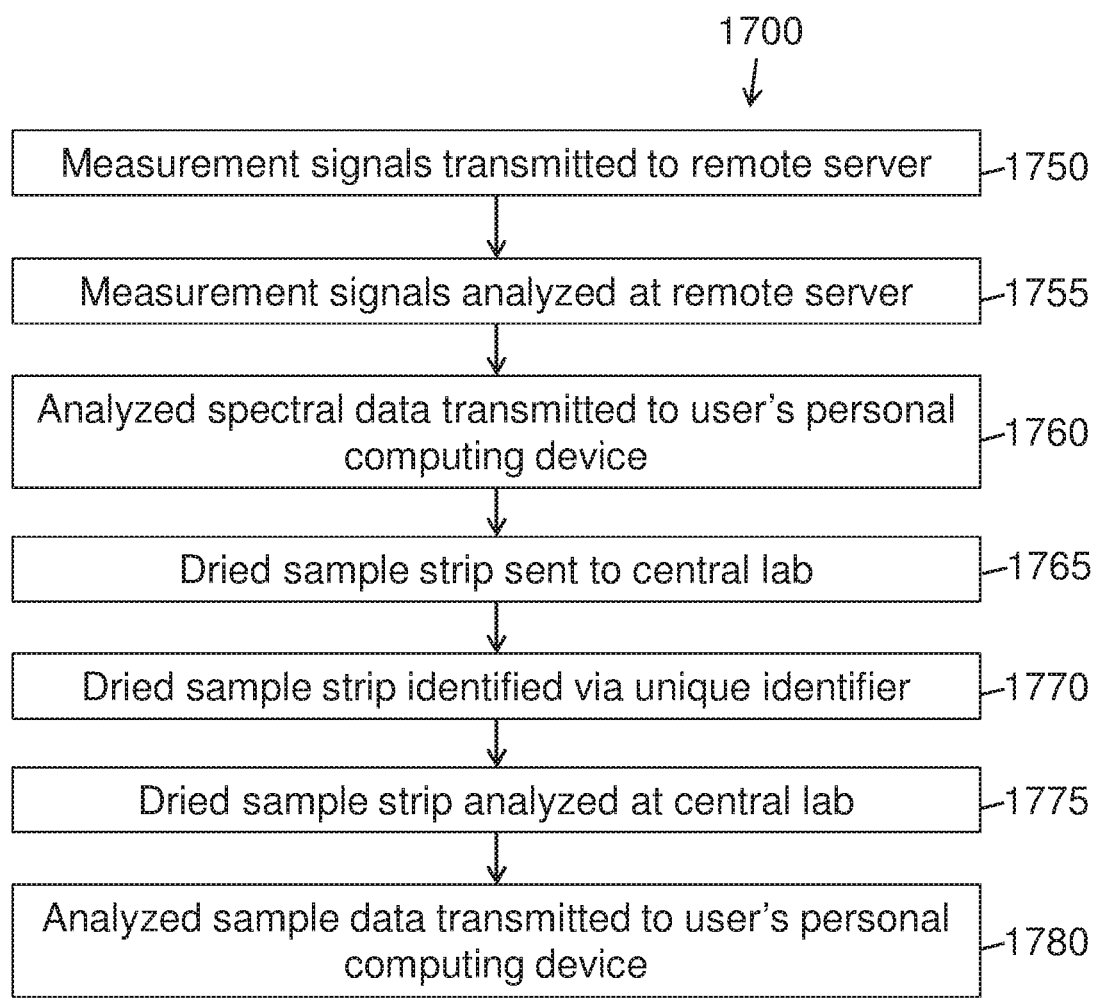

FIG. 17 shows a method 1700 of measuring a sample in accordance with embodiments. At step 1705, aqueous sample may be deposited onto the measurement surface of a sample holder of a measurement apparatus as described herein, over a porous mesh coupled to the measurement surface. At step 1710, excess sample deposited onto the measurement surface can be absorbed by an absorbent member in contact with the porous mesh. At step 1715, the aqueous sample, disposed in the pores of the porous mesh and over the measurement surface, may be measured with total internal reflection (TIR) spectroscopy as described herein. At step 1720, the aqueous sample may be measured with transmission spectroscopy as described herein. At step 1725, the aqueous sample may be measured with diffuse reflection (DR) spectroscopy as described herein. At step 1730, the sample disposed on the measurement surface and absorbed in the absorbent members may be dried, either partially or completely. At step 1735, the dried sample may be measured with TIR spectroscopy. At step 1740, the dried sample may be measured with transmission spectroscopy. At step 1745, the dried sample may be measured with DR spectroscopy.

At step 1750, the measurement signals generated by the measurement apparatus, for example in any of steps 1715-1725 and 1735-1745, may be transmitted from the measurement apparatus to a remote server for analysis, as described herein. At step 1755, the measurement signals may be analyzed at the remote server. At step 1760, the analyzed spectral data may be transmitted from the remote server to a personal computing device of the user.

At step 1765, the dried sample strip, comprising the dried absorbent member having absorbed the sample, may be sent to a central laboratory. At step 1770, the dried sample strip may be identified via a unique identifier of the strip, as described herein. At step 1775, the dried sample strip may be analyzed at the central lab. At step 1780, the analyzed sample data may be transmitted from the central lab to a user's personal computing device.

The steps of method 1700 are provided as an example of a method of measuring a sample, in accordance with embodiments. A person of ordinary skill in the art will recognize many variations and modifications based on the disclosure provided herein. For example, some steps may be added or removed. Some of the steps may comprise substeps, and many of the steps may be repeated. The processor as described herein can be programmed with one or more instructions to perform one or more of the steps of method 1700.

While preferred embodiments of the present disclosure have been shown and described herein, it will be obvious to those skilled in the art that such embodiments are provided by way of example only. Numerous variations, changes, and substitutions will be apparent to those skilled in the art without departing from the scope of the present disclosure. It should be understood that various alternatives to the embodiments of the present disclosure described herein may be employed without departing from the scope of the present invention. Therefore, the scope of the present invention shall be defined solely by the scope of the appended claims and the equivalents thereof.

We claim:

1. An apparatus to measure spectra of a sample, the apparatus comprising:
   an optical waveguide comprising a measurement surface, the optical waveguide configured to transmit measurement light within the optical waveguide via total internal reflection to generate an evanescent wave at the measurement surface; and
   a porous mesh disposed over the measurement surface, the porous mesh comprising a plurality of pores configured to receive a portion of the sample therein, such that the portion of the sample contacts the measurement surface, and the porous mesh comprises an internal standard impregnated therein such that the sample deposited over the porous mesh solvates the impregnated internal standard to a known concentration in the sample,
   wherein the evanescent wave at least partially penetrates the portion of the sample in contact with the measurement surface to measure the spectra of the portion of the sample.

2. An apparatus as in claim 1, wherein the porous mesh comprises a material that imparts no aberrant spectral signal in a spectral region of interest for the sample.

3. An apparatus as in claim 2, wherein the porous mesh comprises a material that imparts no aberrant spectral signal in a mid-infrared spectral range of about 2 µm to about 20 µm.

4. An apparatus as in claim 1, wherein the porous mesh comprises one or more of silver, polyethylene, and polytetrafluoroethylene.

5. An apparatus as in claim 1, wherein the porous mesh comprises a hydrophilic material.

6. An apparatus as in claim 1, wherein each of the plurality of pores is configured to receive a substantially fixed volume of the sample to provide a substantially fixed pathlength of travel of the measurement light.

7. An apparatus as in claim 1, wherein each of the plurality of pores has a diameter of about 0.1 µm to about 20 µm.

8. An apparatus as in claim 7, wherein each of the plurality of pores has a diameter of at least about 10 µm.

9. An apparatus as in claim 7, wherein each of the plurality of pores has a diameter of at least about 5 µm.

10. An apparatus as in claim 7, wherein each of the plurality of pores has a diameter of at least about 1 µm.

11. An apparatus as in claim 1, wherein each of the plurality of pores is sized and shaped to selectively receive a first portion of the sample and selectively exclude a second portion of the sample.

12. An apparatus as in claim 1, wherein the sample comprises whole blood, and wherein the portion of the sample comprises one or more components of the whole blood.

13. An apparatus as in claim 12, wherein the portion of the sample comprises plasma, and does not include cellular components.

14. An apparatus as in claim 12, wherein the portion of the sample comprises plasma and red blood cells, and does not include white blood cells.

15. An apparatus as in claim 12, wherein the portion of the sample comprises plasma, red blood cells, and white blood cells.

16. An apparatus as in claim 12, wherein the portion of the sample comprises red blood cells having cell membranes with rigidity below a predetermined threshold value.

17. An apparatus as in claim 1, wherein the sample is at least partially dehydrated before measurement with the evanescent wave.

18. An apparatus as in claim 1, wherein the sample comprises the internal standard at the known concentration, the internal standard having a distinct spectral signal in a spectral region of interest for the sample.

19. An apparatus as in claim 18, further comprising a sample collection device having the internal standard impregnated therein, and wherein the sample collected in the sample collection device solvates the impregnated internal standard to the known concentration in the sample.

20. An apparatus as in claim 18, wherein the distinct spectral signal is in a mid-infrared spectral region.

21. An apparatus as in claim 1, further comprising one or more absorbent members in contact with the porous mesh to absorb excess sample.

22. An apparatus as in claim 21, wherein the one or more absorbent members comprise one or more blotting papers.

23. An apparatus as in claim 21, wherein the one or more absorbent members are disposed underneath the porous mesh.

24. An apparatus as in claim 23, wherein the porous mesh comprises a first end disposed laterally with respect to the optical waveguide and a second end opposite the first end, and wherein a first absorbent member is disposed underneath the porous mesh near the first end, and a second absorbent member is disposed underneath the porous mesh near the second end.

* * * * *